(12) United States Patent
Sprague

(10) Patent No.: US 7,366,621 B2
(45) Date of Patent: *Apr. 29, 2008

(54) PROGRAM PRODUCT TO MEASURE DENSITY, SPECIFIC GRAVITY, AND FLOW RATE OF FLUIDS

(75) Inventor: James L. Sprague, Dhahran Camp (SA)

(73) Assignee: Saudi Arabian Oil Company, Dhahran (SA)

( * ) Notice: Subject to any disclaimer, the term of this patent is extended or adjusted under 35 U.S.C. 154(b) by 9 days.

This patent is subject to a terminal disclaimer.

(21) Appl. No.: 11/187,563

(22) Filed: Jul. 22, 2005

(65) Prior Publication Data

US 2005/0273278 A1    Dec. 8, 2005

Related U.S. Application Data

(63) Continuation-in-part of application No. 10/856,492, filed on May 28, 2004, now Pat. No. 6,957,586.

(60) Provisional application No. 60/495,743, filed on Aug. 15, 2003.

(51) Int. Cl.
*G06F 19/00* (2006.01)
*G01F 1/32* (2006.01)

(52) U.S. Cl. .............. 702/45; 73/54.04; 73/861.02; 73/861.22; 366/17

(58) Field of Classification Search ............. 702/45, 702/50, 51, 55, 100, 137; 73/861.02, 861.22, 73/861.24, 861.65, 861.66, 152.18, 54.4; 366/17

See application file for complete search history.

(56) References Cited

U.S. PATENT DOCUMENTS 4,226,542 A * 10/1980 Black et al. ............. 366/17

(Continued)

FOREIGN PATENT DOCUMENTS

EP    0 465 182 A2    1/1992

(Continued)

OTHER PUBLICATIONS

Rosemount, Rosemount 485 Annubar® Primary Flow Element Flow Test Data Book, Jun. 2003, found at www.rosemount.com. (note: blanks pages are as printed in original document).

(Continued)

*Primary Examiner*—John Barlow
*Assistant Examiner*—John Le
(74) *Attorney, Agent, or Firm*—Bracewell & Giuliani LLP

(57) ABSTRACT

Program product to measure fluid flow characteristics in a pipeline is provided. A vortex-shedding body is positioned within the pipeline to form vortices. A vortex meter can include a vortex frequency sensor to measure the frequency of the vortices to determine the volumetric flow rate. A differential pressure meter positioned adjacent the vortex-shedding body can produce a differential pressure meter flow rate signal indicative of the density of fluid when flowing through the pipeline. A thermal flow meter positioned adjacent the vortex-shedding body can produce a mass flow rate signal indicative of the mass flow rate of fluid when flowing through the pipeline. The program product can include instructions for a fluid characteristic determiner to perform the operations of processing measured and sensed signals to produce an output of a volumetric flow rate, a flowing fluid density, and a mass flow rate to be displayed on a fluid characteristic display.

20 Claims, 15 Drawing Sheets

U.S. PATENT DOCUMENTS

| | | | |
|---|---|---|---|
| 4,404,858 A | 9/1983 | Blechinger | |
| 4,455,877 A | 6/1984 | Blechinger et al. | |
| 4,523,477 A | 6/1985 | Miller | |
| 5,005,426 A | 4/1991 | Lew | |
| 5,020,373 A | 6/1991 | Kamiunten et al. | |
| 5,121,658 A | 6/1992 | Lew | |
| 5,152,181 A * | 10/1992 | Lew | 73/861.02 |
| 5,230,245 A | 7/1993 | Kamiunten et al. | |
| 5,461,930 A | 10/1995 | Farchi et al. | |
| 5,654,502 A * | 8/1997 | Dutton | 73/152.18 |
| 6,196,058 B1 * | 3/2001 | Chen | 73/54.04 |
| 6,298,734 B1 * | 10/2001 | Storer et al. | 73/861.22 |
| 6,412,353 B1 | 7/2002 | Kleven et al. | |
| 6,484,590 B1 | 11/2002 | Kleven et al. | |
| 6,938,496 B2 * | 9/2005 | Koudal et al. | 73/861.22 |
| 2003/0061887 A1 | 4/2003 | Koudal et al. | |

FOREIGN PATENT DOCUMENTS

| | | |
|---|---|---|
| EP | 0 763 718 A1 | 3/1997 |
| GB | 1463507 A | 2/1977 |
| GB | 2 212 277 A | 7/1989 |
| RU | 2071595 C1 | 1/1997 |

OTHER PUBLICATIONS

Yamatake Corporation, Article Titled "Heat Value Gas Chromatograph Specifications"; Rev. 6, Dec. 2001, found at www.yamatake.co.jp.

Solartron Mobrey Limited, Data Sheet B1253, titled "Solartron Gas Density & Specific Gravity Products", Feb. 2001, found at www.solartronmobrey.com, .

* cited by examiner

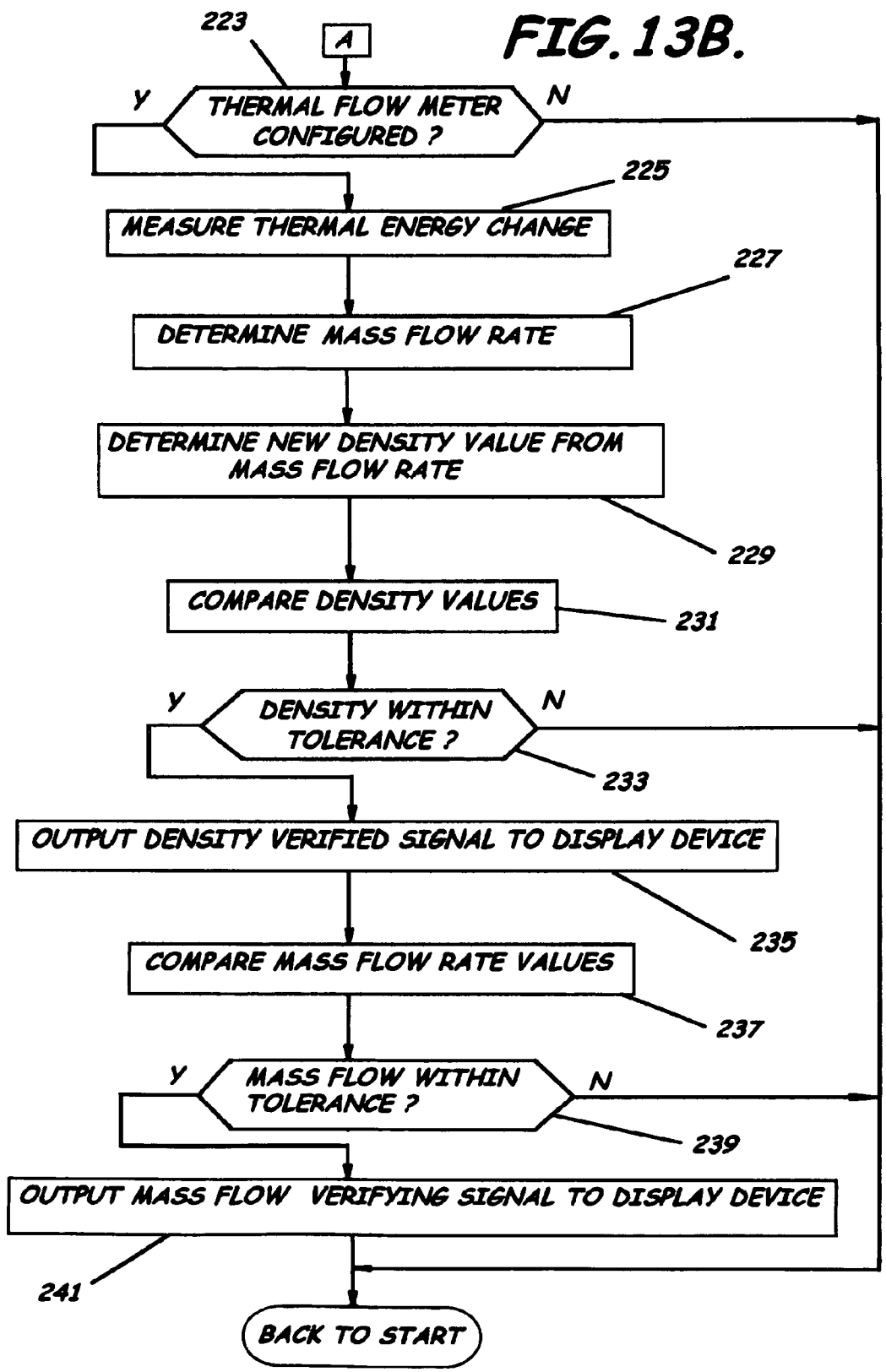

PROGRAM PRODUCT TO MEASURE DENSITY, SPECIFIC GRAVITY, AND FLOW RATE OF FLUIDS

CROSS REFERENCE TO RELATED APPLICATIONS

This is a continuation-in-part patent application which claims priority to and the benefit of U.S. patent application Ser. No. 10/856,492, filed on May 28, 2004 now U.S. Pat. No. 6,957,586, titled "System to Measure Density, Specific Gravity, and Flow Rate of Fluids, Meter, and Related Methods," which claims priority to and the benefit of U.S. Provisional Patent Application No. 60/495,743 filed on Aug. 15, 2003, all of which are incorporated herein by reference in their entireties.

BACKGROUND OF THE INVENTION

1. Field of the Invention

The present invention relates generally to flow meters. In more specific aspects, the present invention relates to the measurement of the density, specific gravity, and flow rate of flowing fluids, systems, apparatus, program product and methods.

2. Description of the Related Art

Many industrial facilities feed fuel gases to their industrial combustion processes. Particularly, these fuel gases tend to be low molecular weight hydrocarbon fuel gases. These fuel gases typically have a constantly changing hydrocarbon composition. To maintain an efficient fuel-air ratio combustion control, the BTU content, must be known. The BTU content of the fuel gas can be determined directly via a BTU analysis or the BTU content can be inferred from the fuel gas density or specific gravity. Both direct BTU measurement and density measurement techniques are typically expensive and complex. Most industrial combustion processes with varying composition fuel gases use either gas chromatographs to measure the BTUs or vibrating spool densitometers to determine fuel gas density. However, both of these instruments, though accurate, are very costly and require highly skilled technicians to conduct frequent maintenance.

The typical gas chromatographs can provide 0.1% BTU measurement accuracy but are very complex. For example, the Yamatake Model HGC303 Heat Value Gas Chromatograph manufactured by Yamatake Corporation, located in Shibuya-ku, Tokyo, uses a gas chromatography measuring principle to measure heat value of natural gas and is used generally for the purpose of natural gas consumption management. A heated filament is contained in a stainless steel block of the detector. The individual components of the gas sample are separated in chromatograph columns and passed through a detector. Each component of the gas that passes through the detector transfers heat from the measuring thermistor to the wall of the block. The amount of heat transferred is dependent on the concentration and thermal conductivity of the gas component. The resistance of the measuring thermistor changes relative to the reference thermistor. This change is converted to a voltage.

A vibrating spool densitometer can also theoretically obtain a gas density stated accuracy as high as 0.1%. They require, however, specialized sampling and discharge arrangements. For example, the Solartron B1253 manufactured by Solartron Mobrey Limited, located in Slough Berks England, is a gas density meter whose measuring principle is based on the use of a resonating cylinder. The pipeline containing the gas is tapped to extract a continuous gas sample to be passed through a density transducer. The density of the gas flowing through a transducer changes the natural resident frequency of the cylinder. By maintaining this vibration and measuring its frequency electronically, the density of the gas which is directly related to mass flow can be determined.

Flame BTU analyzers can give between 0.4-2.0% BTU measurement accuracy but are also very complex. For example, the COSA 9600 manufactured by COSA Instrument located in Norwood N.J. is a flame BTU analyzer whose measuring principle, typically called the "residual oxygen measurement method," is based on the analysis of the oxygen content of a sample of fuel gas after combustion. A continuous sample of gas is mixed with dry air at a precise ratio selected dependent upon the BTU range of the gas to be measured. The fuel-air mixture is oxidized in a combustion furnace in the presence of a catalyst at 800° C., and an oxygen concentration of the combustion sample is measured by a zirconia oxide cell. The residual oxygen provides a measurement of the combustion air requirement of the sample gas.

Coriolis meters can be used for fuel gas density measurement while being somewhat less complex for certain types of fuel gases. The measurement of the mass flow rate in a Coriolis meter is based on the principle of causing a medium to flow through a flow tube inserted in the pipe and vibrating during operation, whereby the medium is subjected to Coriolis forces. The latter causes the inlet-side and outlet-side portions of the flow tube to vibrate out of phase with respect to each other. The magnitude of these phase differences is a measure of the mass flow rate. The vibrations of the flow tube are therefore sensed by use of two vibration sensors positioned at a given distance from each other along the flow tube and converted by these sensors into measurement signals having a phase difference from which the mass flow rate is derived. The meters, however, typically cannot accurately measure low molecular weight gas density.

There is a need to easily and without an excessively complex instrument measure density and flow rate of low molecular weight fuel gases fed to combustion boilers. Vortex Shedding Flow Meters are fairly simple instruments requiring little maintenance. Fluid passing around a bluff body produces a stream of vortices with a generation rate which is proportional to the flow rate of the fluid. A sensor responsive to the vortices produces a signal having a frequency representing the flow rate. The flow rate signal can then be used for calculating the resulting volumetric flow rate of the fluid in the pipe. The measure of fluid flow rate for the Vortex Shedding Flow Meter, however, is independent of density. Thus, it is not possible to derive density or mass flow rate from the volumetric flow rate measurement, alone, especially where the fluid is in a gaseous form. An Averaging Pitot Tube and a Thermal Flow Meter, however, both measure flow rate dependent upon fluid density.

Various devices trying to apply this principle have been proposed. For example, U.S. Pat. No. 4,523,477, by Miller, titled "Planar-Measuring Vortex-Shedding Mass Flow Meter" describes placing up to two dynamic pressure ports of a differential pressure measuring device at the upstream surface of the vortex-shedding body and placing a static pressure port along the circumference of the production pipe housing the vortex meter in a position traverse to the fluid flow and within one-half of the vortex wavelength of the dynamic pressure port. The dynamic pressure port passageways extend through the production pipe and are coupled via a manifold connector on the external surface of the production pipe. A divider circuit divides the electrical signal of the differential pressure measuring device by a flow rate signal obtained from the velocity sensing portion of the device to obtain mass flow. Because it requires breaching the production pipe for each of the static and dynamic ports of the differential pressure measuring device, however, the device, is complex to install. Additionally, it is not sufficiently accurate because it does not directly provide pressure and temperature compensated density.

Also, for example, in GB 2,212,277A, by Jackson et al., titled "Gas Flow Meter," the meter calculates gas density in order to compute the values for mass flow. The gas density, however, is not continuously measured through all flow ranges but is instead computed based on charted data. The thermal flow meter portion, separate from the vortex flow meter portion, only measures mass flow at low flow rates and the vortex meter portion only measures velocity at high flow rates with an overlap region in which the outputs of the two portions of the device are combined to provide a calculated gas density to determine mass flow rate for the high flow rates. Temperature is monitored and can sometimes be applied to attempt to correct the calculated gas density during an interim where the flow velocity is outside the overlap region, and thus, unable to provide for a truly updated gas density calculation. The device does not have a combined unit that measures fluid density at substantially all operational flow rates, and therefore cannot provide for a continuously updated gas density much less a continuously updated gas density output. Also, the device is truly two separate devices as the separate thermal flow meter is positioned in a separate meter passage than that of the vortex flow meter and is thus more difficult and complex to install.

Accordingly, the Applicant has recognized that there still exists a need for a simple, no-moving-part, and low-cost industrial metering instrument capable of measuring and outputting process fluid density as well as flow rate. Applicant has especially recognized the need for an integrated metering instrument accurate for measuring low molecular weight fuel gases fed to combustion process. Applicant also recognized a need for a metering instrument for both measuring and outputting volumetric flow rate, mass flow rate, and density of a fuel gas without resorting to a complex device. Applicant has further recognized that an accuracy of approximately 2-4% for a density meter can be acceptable as a trade-off for having less costly, less maintenance intensive integrated metering instrument, rather than a separate and complex analyzer.

SUMMARY OF THE INVENTION

In view of the foregoing, embodiments of the present invention advantageously and uniquely integrate well-known industrial flow meter operating principles into a single industrial instrument. Embodiments of the present invention provide a simple, low-cost flow metering components integrated into a single flow metering device capable of measuring process fluid density as well as flow rate. Embodiments of the present invention also advantageously provide a system to measure fluid flow characteristics in a pipeline to provide a volumetric flow rate, a mass flow rate, and density of flowing fluid. Embodiments of the present invention further advantageously provide a process density meter to measure fluid flow characteristics in a pipeline. Embodiments of the present invention advantageously provide a method of measuring flowing fluid characteristics in a pipeline. Further, embodiments of the present invention advantageously provide a program product to measure flowing fluid characteristics in a pipeline.

More particularly, embodiments of the present invention include a computer readable medium that is readable by a computer for measuring fluid flow characteristics in a pipeline. For example, according to an embodiment of the present invention, a computer readable medium can include a set of instructions that, when executed by a computer, cause the computer to perform the operation of calculating a density indicative of flowing fluid density and a mass flow rate indicative of flowing fluid mass flow rate responsive to a volumetric flow rate and a differential pressure meter flow rate signal. The volumetric flow rate of fluid flowing in the pipeline, for example, can be determined by a vortex meter positioned adjacent a vortex shedding bluff body positioned in the pipeline. The vortex shedding body can have an upstream surface including at least one total pressure inlet port and a downstream surface having at least one static pressure inlet port. The differential pressure meter flow rate signal for the flowing fluid, for example, can be determined by a differential pressure meter positioned adjacent the vortex shedding bluff body. Advantageously, the fluid can be in the form of a plurality of various types of liquids or gases, such as a combustion gas, or a mixture thereof.

The instructions can also include those to perform the operation of conditioning the density to form a temperature and pressure compensated density responsive to a received or measured ambient temperature and static pressure of the flowing fluid. The ambient temperature, for example, can be received from an ambient temperature sensor electrically connected to a thermal flow meter positioned adjacent the vortex shedding bluff body. The static pressure, for example, can be received from the differential pressure meter. Similarly, the instructions can also include those to perform the operation of conditioning the mass flow rate to form a temperature and pressure compensated mass flow rate responsive to the ambient temperature and static pressure. Further, the volumetric flow rate, the conditioned density, and the conditioned mass flow rate can be displayed alone or in combination on, e.g., a fluid characteristic display.

In another embodiment of the present invention, a computer readable medium is provided that is readable by a computer to measure fluid flow characteristics in a pipeline having a set of instructions that, when executed by the computer, cause the computer to perform the operations of determining a fluid flow rate and a volumetric flow rate responsive to a vortex frequency shedding rate of a vortex shedding bluff body, and determining a specific gravity of the flowing fluid responsive to the volumetric flow rate and a differential pressure meter flow rate signal. According to the embodiment, for example, the differential pressure meter flow rate signal can be proportional to a differential pressure formed by the vortex-shedding bluff body. Particularly, the differential pressure can be formed across the upstream and at least one of the downstream surfaces of the vortex-shedding bluff body. The instructions can also include those to perform the operations of determining density of the flowing fluid responsive to the specific gravity, and providing data to display the density and the volumetric flow rate on, e.g., a fluid characteristic display positioned to receive the density and the volumetric flow rate.

In another embodiment of the present invention, a computer readable medium is provided that is readable by a computer for measuring fluid flow characteristics in a pipeline having a set of instructions that, when executed by the computer, cause the computer to perform the operations of calculating a density indicative of flowing fluid density of the flowing fluid responsive to a received or measured volumetric flow rate and thermal flow meter flow rate, and providing data to display the volumetric flow rate, the density, and the mass flow rate. The volumetric flow rate of fluid flowing in the pipeline, for example, can be received from/measured by a vortex meter positioned adjacent to a vortex shedding bluff body positioned in the pipeline. In this embodiment, the vortex shedding bluff body can have an upstream surface, a plurality of downstream surfaces, a thermal sensor fluid passageway extending between the upstream surface and at least one of the plurality of downstream surfaces, with at least one thermal sensor positioned within the thermal sensor fluid passage way. The mass flow rate for the flowing fluid, for example, received from/measured by a thermal flow meter positioned adjacent the vortex shedding bluff body and electrically connected to an ambient temperature sensor and the at least one thermal sensor.

Advantageously embodiments of the present invention can provide an instrument intended for use in industrial combustion processes using low molecular weight hydrocarbon fuel gases, but may be used in any industrial process where simple, low-cost, and maintenance free density and fluid flow rate measurements are desired.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and therefore are not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments. Note, the term "adjacent" as used herein refers to a position that is within, on, or near the object referenced.

As illustrated in FIGS. 1-14, embodiments of the present invention advantageously provide a system, meter, and methods for measuring fluid flow characteristics in a pipeline. In particular, the flow characteristics of primary interest relate to industrial combustion processes using low molecular weight hydrocarbon fuel gases but can be used in other processes where density and flow rate measurements are required. Of interest, many industrial facilities feed fuel gases to their combustion processes, for example, combustion boilers. These fuel gases constantly change in hydrocarbon composition. For example, the fuel gases may include varying percentages of methane, ethane, and propane. To maintain efficient fuel-air ratio combustion control, as a minimum, a user must know the BTU content, which can be derived from hydrocarbon density. Ideally, the user would also prefer both volumetric flow rate and mass flow rate. In an embodiment of the present invention, the system 30 includes a pipeline 31, a process density meter 33 positioned at least partially within the pipeline, and a fluid characteristics display device 35 positioned to display to the user volumetric flow rate, flowing fluid density, and mass flow rate of flowing fluid within the pipeline 31.

Figure 1:
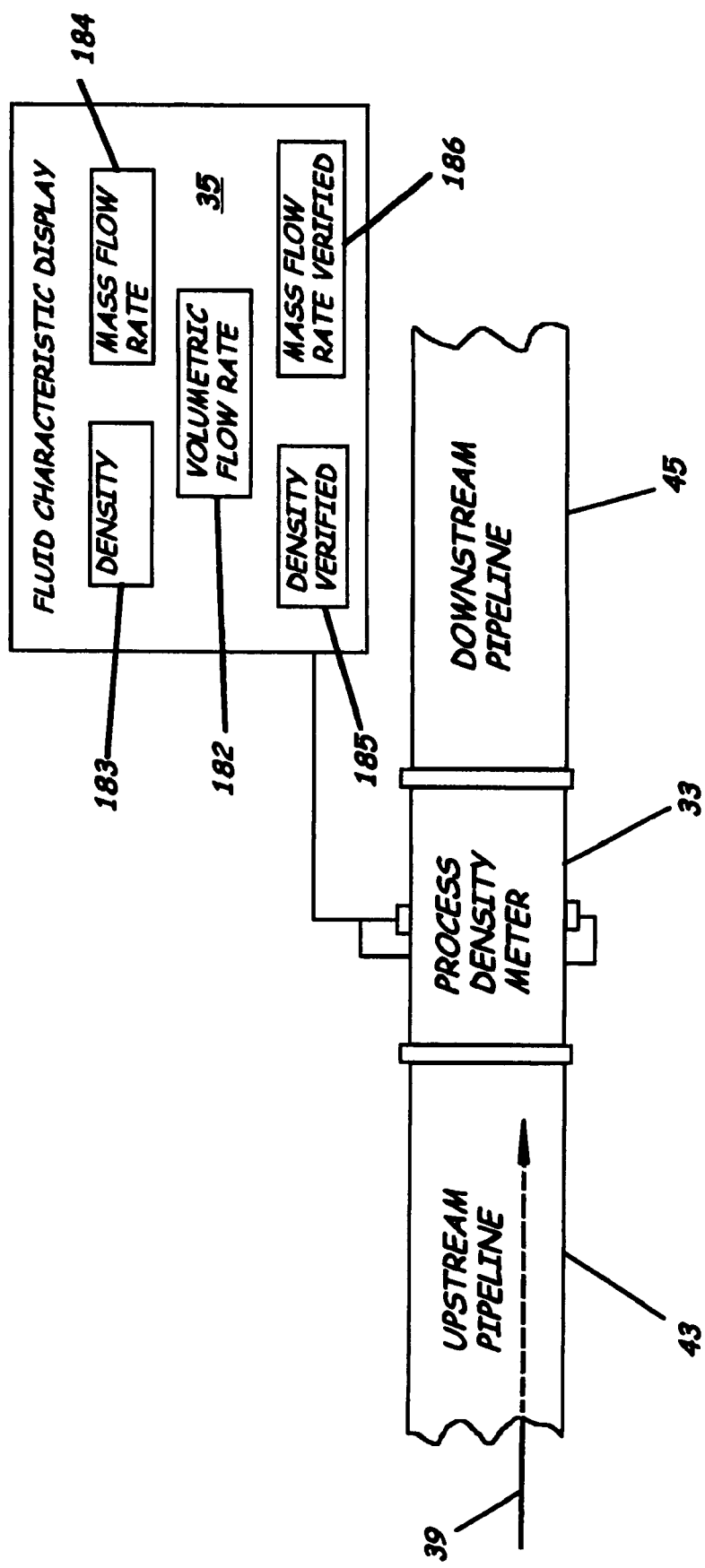
FIG. 1 is a schematic view of a system for measuring fluid flow characteristics in a pipeline according to an embodiment of the present invention.
Figure 2:
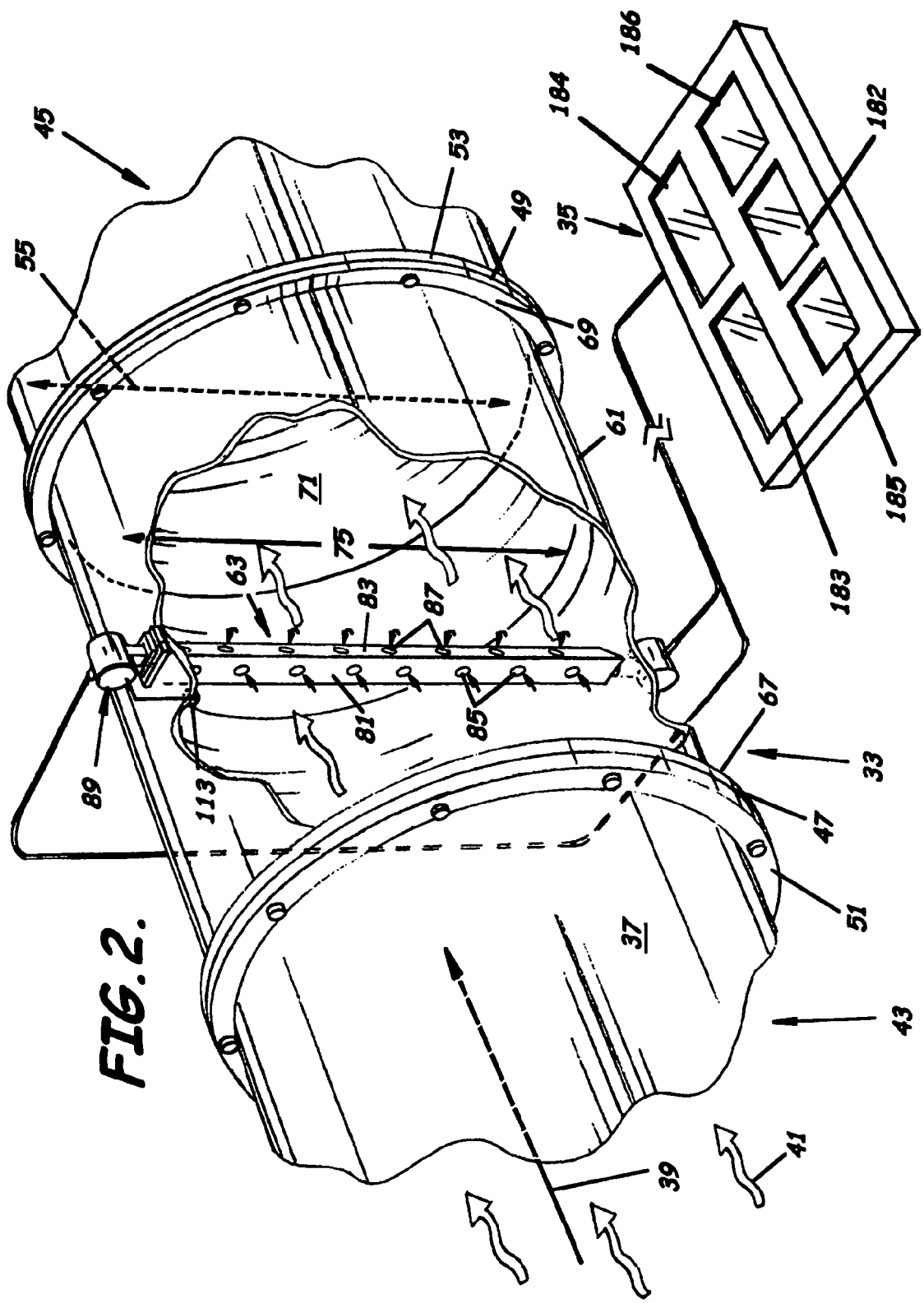
FIG. 2 is a prospective sectional view of a system for measuring fluid flow characteristics in a pipeline according to an embodiment of the present invention.

As perhaps best shown in FIGS. 1 and 2, the pipeline 31 includes a fluid passageway 37 having a longitudinal axis 39 to transport fluid 41. The fluid 41 can be in the form of a plurality of various types of liquids or gases, such as a combustion gas, or a mixture thereof. The pipeline 31 can be of varying lengths and diameters according to the needs of a user. The pipeline 31 is well known to those skilled in the art and generally includes upstream and downstream sections 43, 45, each connected at an interface 47, 49, using an attachment assembly including fasteners such as a plurality of bolts positioned to connect a flange 51 on the downstream end of the upstream section 43 with a flange 53 on the upstream end of the downstream section 45. The pipeline 31 has a predetermined inner diameter 55 and cross-sectional area.

Figure 3:
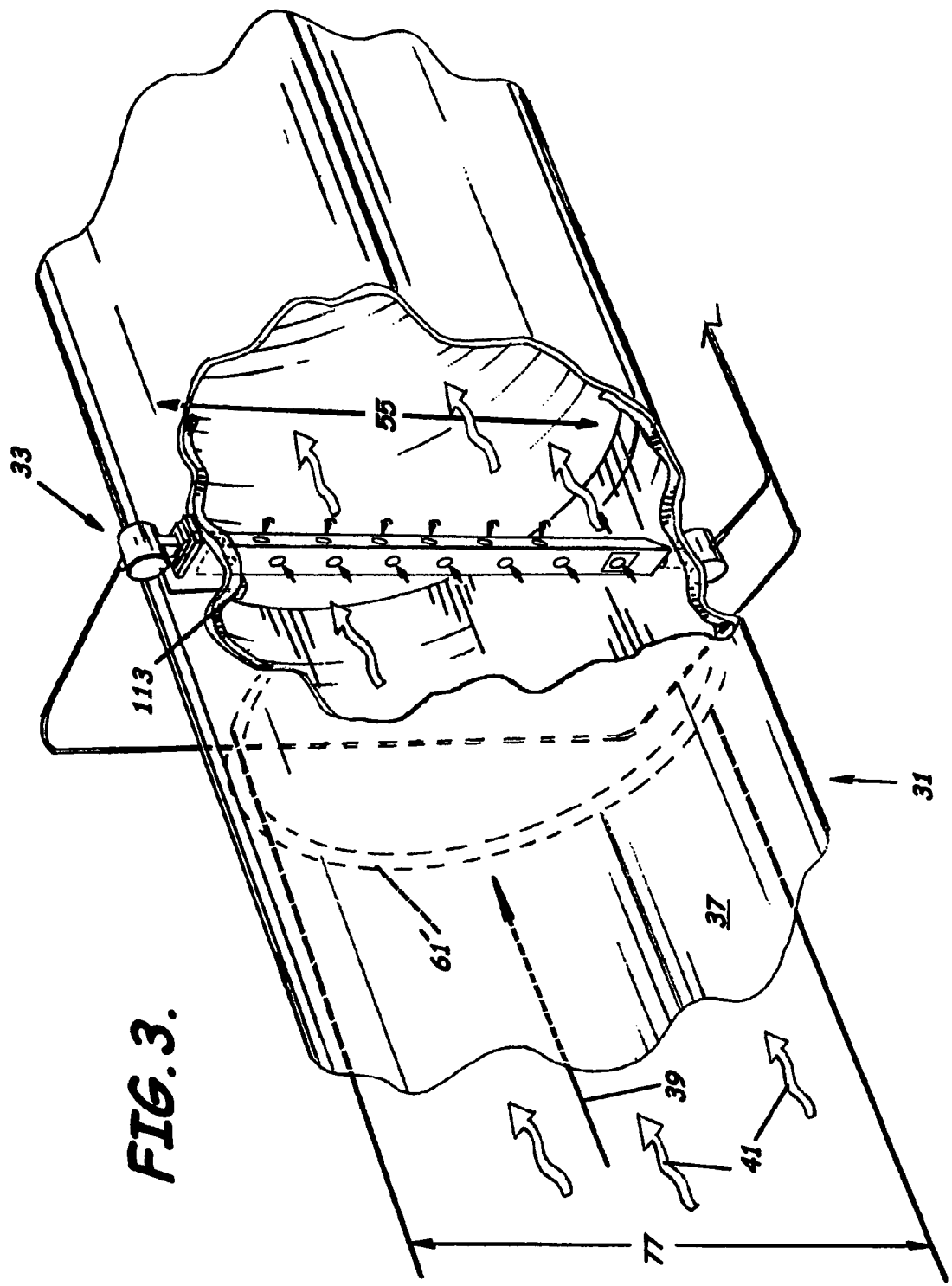
FIG. 3 is a prospective sectional view of a system for measuring fluid flow characteristics in a pipeline according to another embodiment of the present invention.
Figure 4:
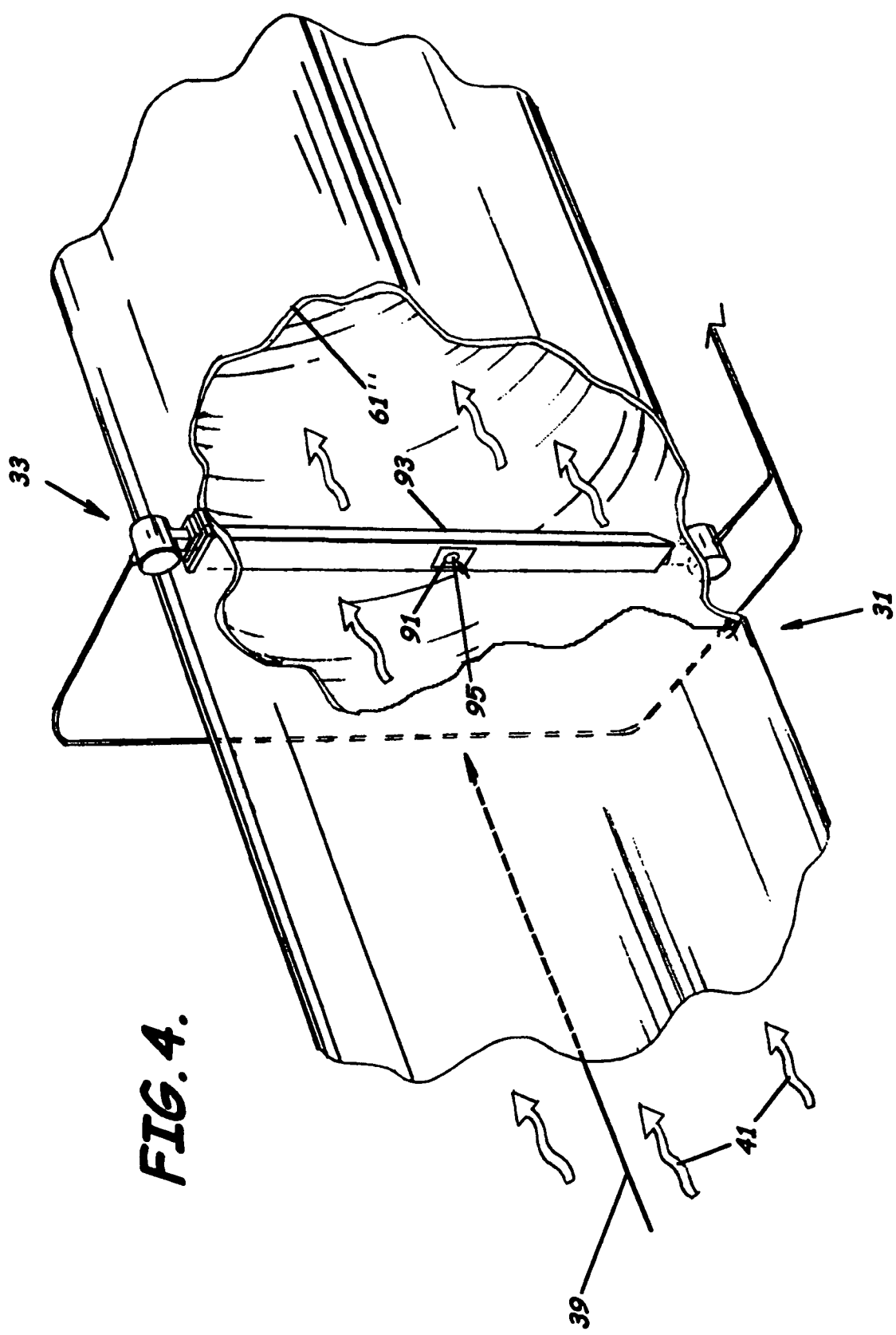
FIG. 4 is a prospective sectional view of a system for measuring fluid flow characteristics in a pipeline according to another embodiment of the present invention.

The process density meter 33 is positioned at least partially within the pipeline 31. In the typical configuration, the bulk of the electronics, other than sensors (described below) are located external to the pipeline 31 and the sensors and related equipment are located within the confines of the pipeline 31. The process density meter 33 can include a process density meter housing 61 to house the sensors and related equipment and to support a vortex-shedding body 63 of a vortex measuring device 65 within the flowing fluid 41 of the pipeline 31. In an embodiment of the present invention, the process density meter housing 61 includes as a first end 67, a second end 69, and a fluid passageway 71 extending therebetween. The process density meter housing 61 is preferably positioned coaxially between a pair of upstream and downstream sections 43, 45, of the pipeline 31. The process density meter housing 61 is adapted to connect between the upstream and downstream sections 43, 45, through use of a connection assembly as known and understood by those skilled in the art. In one configuration, the process density meter housing 61 is sized to match a section of the pipeline 31 such that the process density meter housing 61 has an inner diameter 75 substantially the same as the predetermined inner diameter 55 of the pipeline 31. Functionally, the process density meter housing 61 becomes part of the pipeline 31 and is in fluid communication with flowing fluid 41 within the pipeline 31. Alternatively, as best shown in FIG. 3, the process density meter housing 61' can be instead sized to fit within the section of the pipeline 31. In this configuration, the outer diameter 77 of the process density meter housing 61' is preferably substantially the same diameter as the predetermined inner diameter 55 of the pipeline 31. Also, as best shown in FIG. 4, instead of supplying a separate process density meter housing, the sensors and associated equipment (described in detail below) can be positioned and supported within a section of the pipeline 31. In this configuration, the selected section pipeline 31 functionally becomes the process density meter housing 61".

FIGS. 1-9 illustrate a process density meter 33 including a vortex-shedding body 63 positioned within the pipeline 31. The vortex-shedding body 63 is preferably in the form of a three-dimensional bluff body having an upstream side 81 and a plurality of downstream sides 83, but can be in the form of a two-dimensional bluff body, such as a cylinder (not shown), and still be within the scope of the present invention. The vortex-shedding body 63 is preferably shaped to produce a Reynolds number in excess of approximately 20,000. In one configuration, the vortex-shedding body 63 is adapted to connect to the pipeline 31 or pipeline housing 33 on opposite sides within the fluid passageway of the pipeline 37 or fluid passageway 71 of the pipeline housing 61, as shown above in FIGS. 2-4. Alternatively, the vortex-shedding body 63 need only be connected at one attachment point within the pipeline 31 or pipeline housing 61 and still remain properly supported. The vortex-shedding body 63 can be less than the diameter of the pipeline 31 or pipeline housing 61, however, a more uniform reading of static and dynamic pressures (described later) can be obtained by having the vortex-shedding body 63 full-length.

Figure 5:
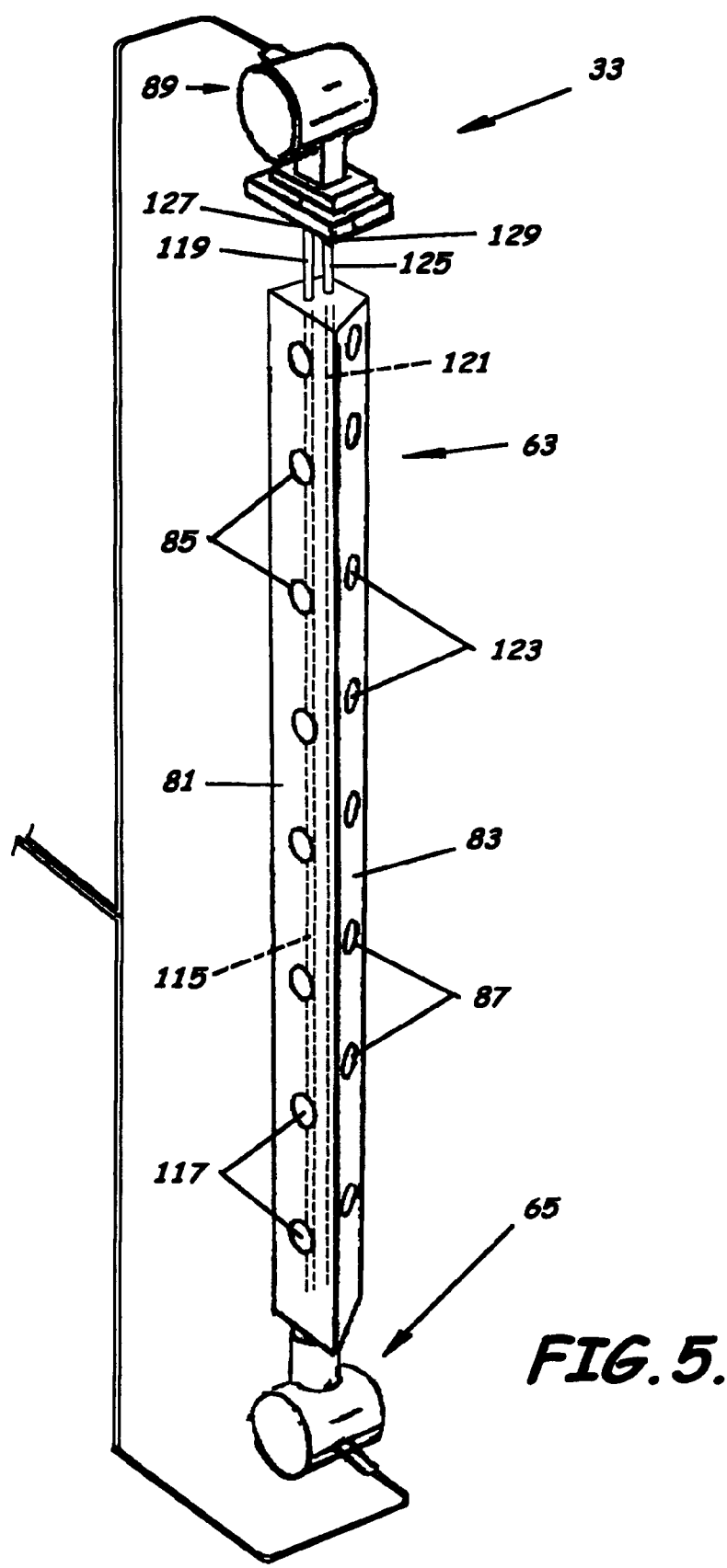
FIG. 5 is a partial perspective sectional view of a process density meter according to an embodiment of the present invention.
Figure 6:
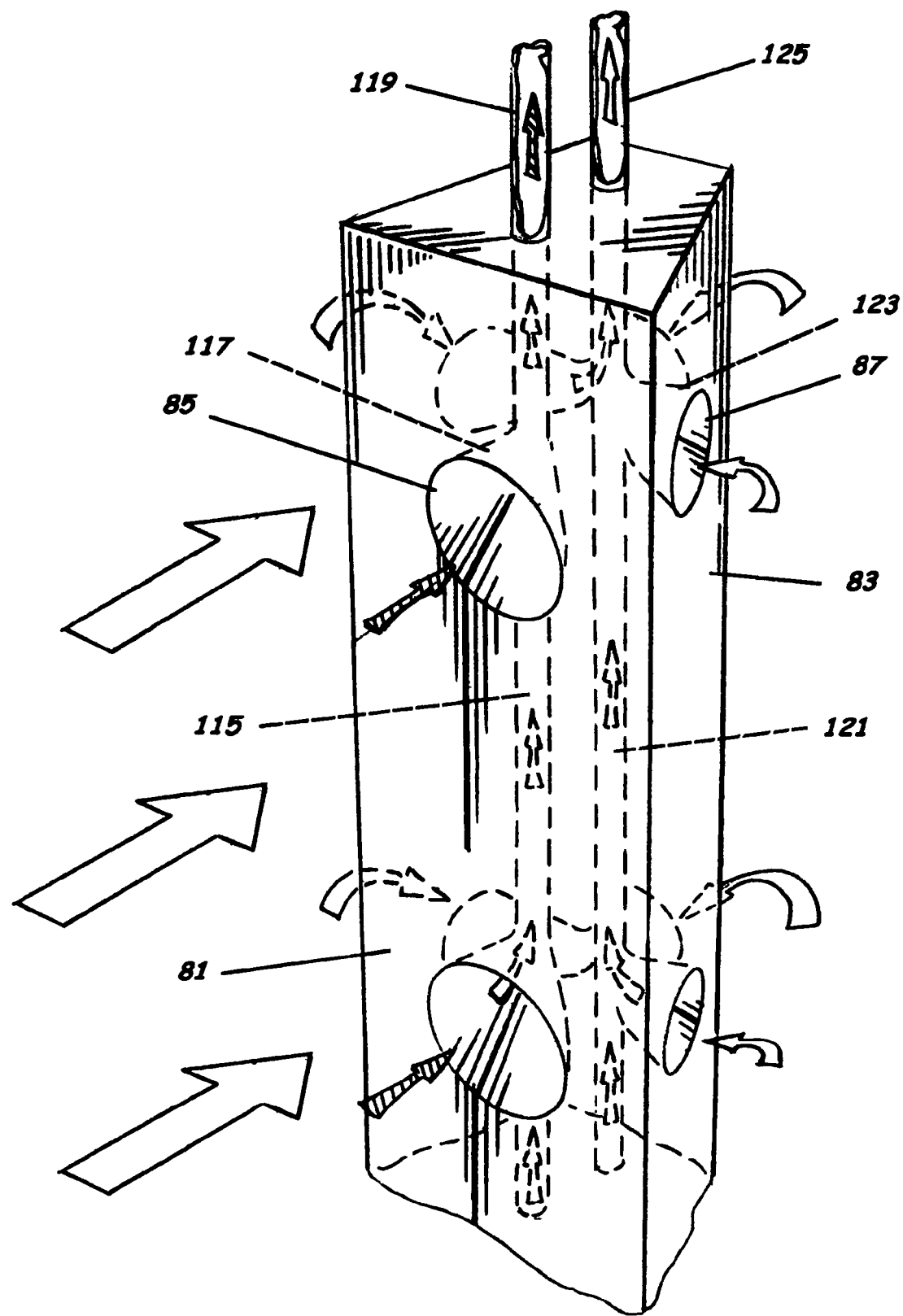
FIG. 6 is a partial perspective sectional view of a section of the vortex shedding body of FIG. 5 according to an embodiment of the present invention.

FIGS. 2, 5, and 6 illustrate a vortex-shedding body 63 including an upstream surface 81 positioned transverse to the longitudinal axis 39 of the pipeline 31 which have or contain a plurality of total pressure inlet ports 85 positioned in the upstream surface 81. The vortex-shedding body 63 also includes a plurality of downstream surfaces 83 which have or contain a plurality of static pressure inlet ports 87 positioned in at least one of the downstream surfaces 83. The total pressure ports 85 and static pressure ports 87 can be used in conjunction with a differential pressure sensing device such as a pitot-type differential pressure meter 89, described below. The plurality of upstream ports 85 and downstream ports 87 provide the ability to average the pressures across the vortex-shedding body 63 within the pipeline 31, thus improving meter accuracy, and serve to resist plugging, minimizing the need for maintenance on the process density meter 33. Having the plurality of downstream surfaces 83, rather than a cylindrical shape, can improve vortex-shedding and delineation between the total and static pressures.

Figure 7:
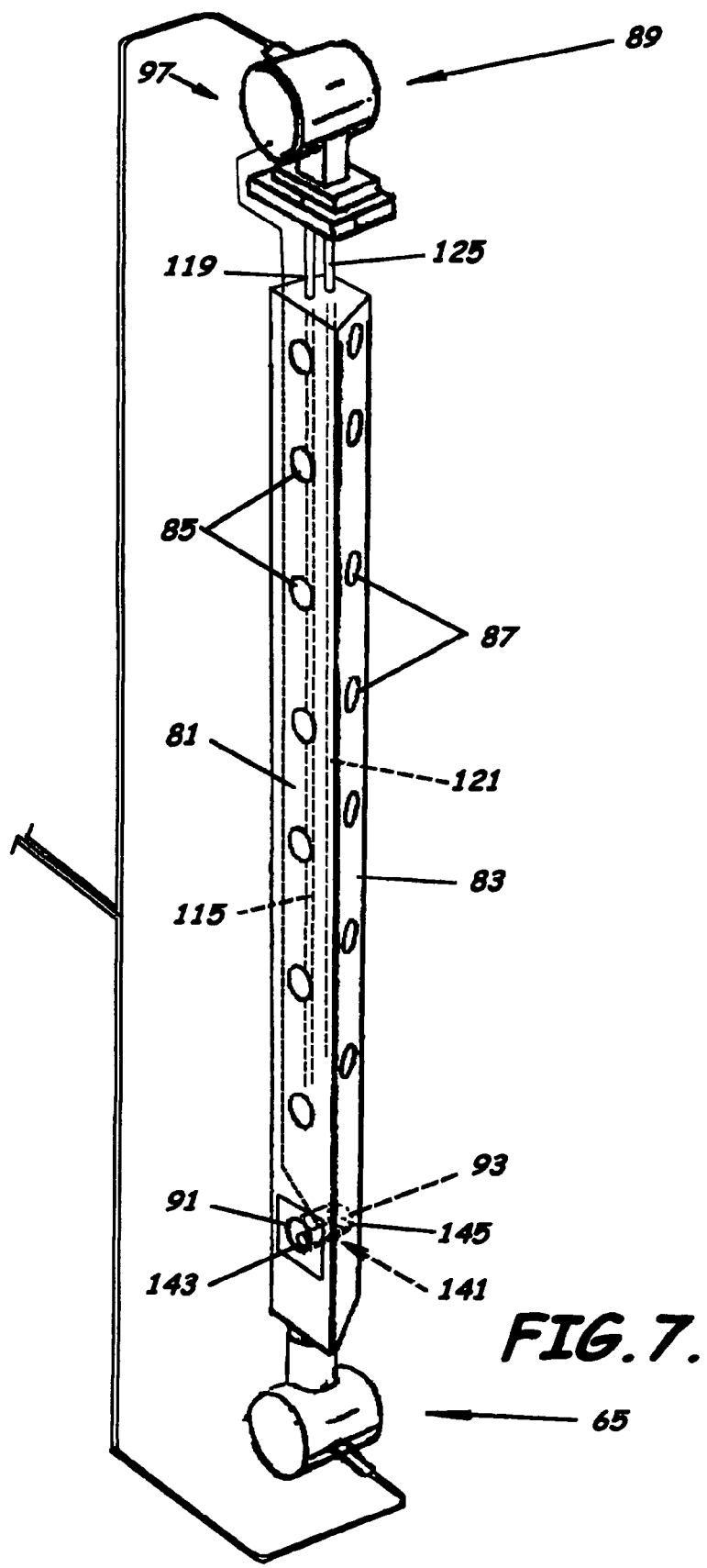
FIG. 7 is a partial perspective sectional view of another embodiment of the process density meter according to another embodiment of the present invention.

In an embodiment of the present invention, as perhaps best shown in FIGS. 2 and 7, the vortex-shedding body 63 also has a thermal sensor inlet port 91, typically positioned in the upstream surface 81, and correspondingly, a thermal sensor outlet port 93 positioned in at least one of the downstream surfaces 83. A fluid passageway 95 extends between the thermal sensor inlet port 91 and the thermal sensor outlet port 93 so that fluid flowing through the pipeline passes therethrough for use with a thermal flow sensing device such as the thermal flow meter 97 (described later).

Figure 10:
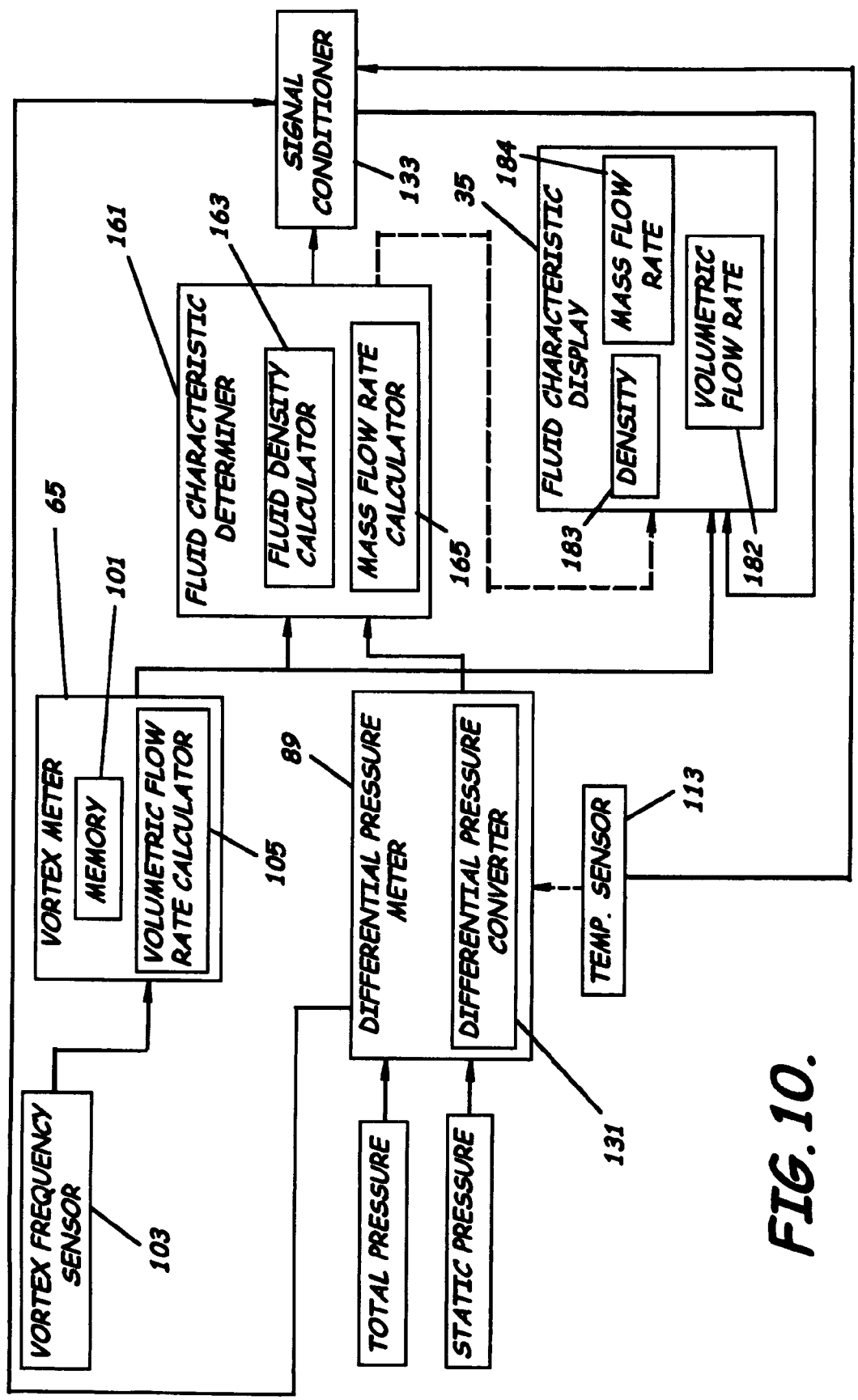
FIG. 10 is a functional block diagram illustrating a basic structure of a process density meter circuit of FIG. 5 according to an embodiment of the present invention.
Figure 11:
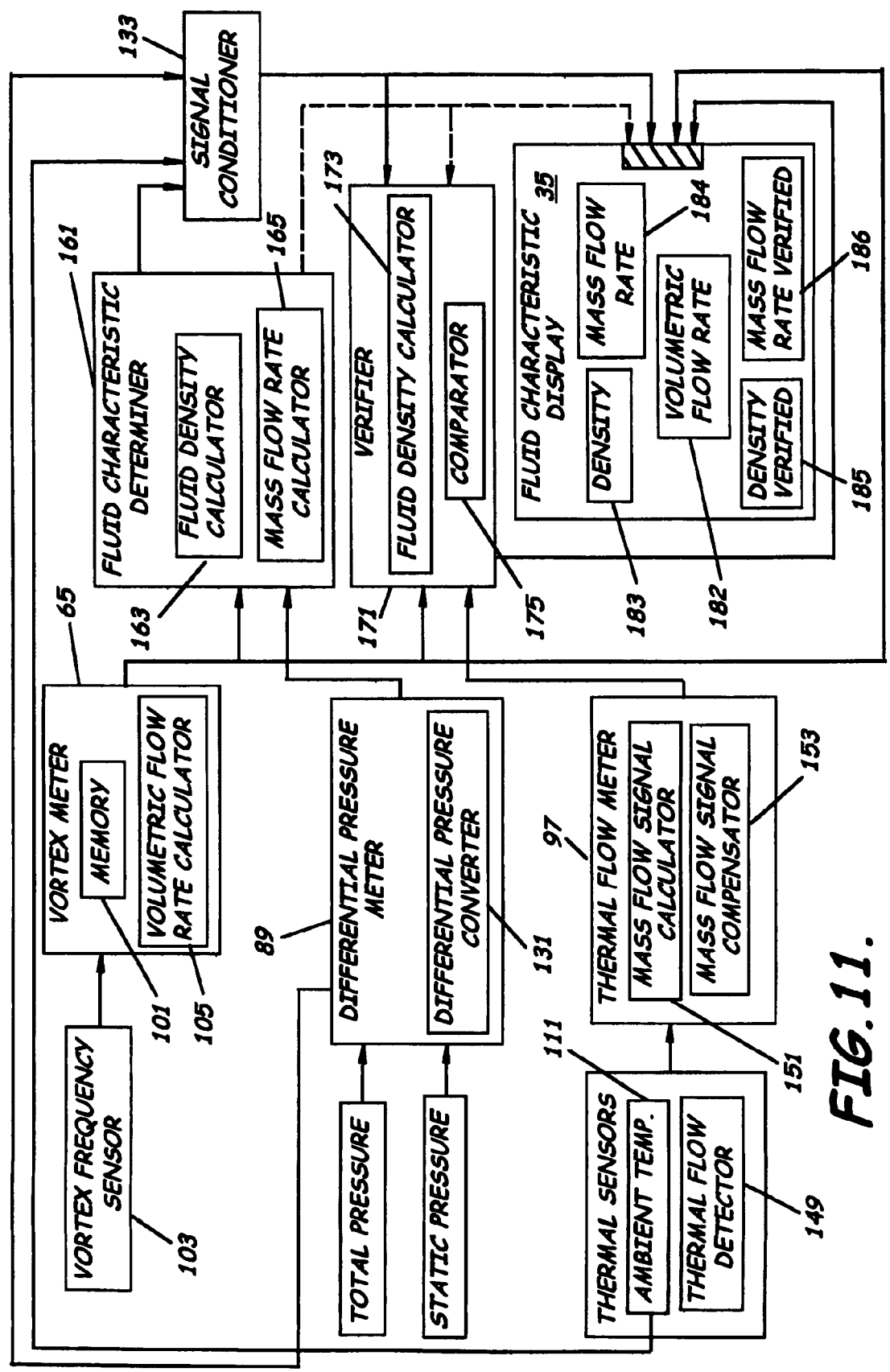
FIG. 11 is a functional block diagram illustrating a basic structure of a process density meter circuit of FIG. 7 according to an embodiment of the present invention.

FIGS. 10 and 11 illustrate a process density meter 33, according to two embodiments of the present invention which also include a vortex measuring device such as a vortex meter 65. The vortex meter 65 measures the frequency of vortices shed from the vortex-shedding body 63 to produce a signal indicative of volumetric fluid flow rate $Q_{vortex}$ within the pipeline 31. The vortex meter 65 includes a memory 101, a vortex frequency sensor 103, and a volumetric flow rate calculator 105. The memory 101 stores pipeline volume data for use by the volumetric flow rate calculator 105. The pipeline volume data generally includes the inner diameter 55 of the pipeline 31 along with other data as known to those skilled in the art necessary to determine cross-sectional area of the inner dimensions of the pipeline 31. The vortex frequency sensor 103, optionally positioned adjacent the vortex-shedding body 63, senses the frequency of vortices shed by the vortex-shedding body 63 to thereby produce a fluid flow rate signal responsive to the frequency of vortices shed by the vortex-shedding body 63. The vortex frequency sensor 103 is preferably in the form of a strain gauge or pressure transducer positioned in the vortex-shedding body 63 or within the pipeline housing 33 but can embody other forms which may require different positioning, such as downstream of the vortex-shedding body 63, and still be within the scope of the present invention. The volumetric flow rate calculator 105, positioned to receive the pipeline volume data stored in the memory 101 and the flow rate signal from the vortex frequency sensor 103, calculates a volumetric flow rate signal indicative of volumetric flow rate of fluid 41 when flowing through the pipeline 31.

In a preferred configuration, the volumetric flow rate calculator 105 of the vortex meter 65 further is positioned to receive an ambient temperature signal and a static pressure signal. The ambient temperature signal can be either from an ambient temperature sensor 111 associated with a thermal flow meter 97 (described later) or a separate ambient temperature sensor 113 (FIG. 2). The static pressure signal can be either from a differential pressure flow meter 89 (describe later) or a separate static pressure sensor (not shown). The ambient temperature and static pressure can be used by the vortex meter 65 to produce a temperature and pressure compensated volumetric flow rate signal v by compensating the flow rate signal for the temperature and pressure experienced by the vortex frequency sensor 103. A volumetric flow rate $Q_{vortex}$ can be calculated using the formula:

$$Q_{vortex} = A \times v,$$

where A is the cross-sectional area of the portion of pipeline where flow rate is measured and v is the fluid velocity. Additionally, if the inner dimension of the pipeline housing is not substantially the same as the inner dimension of the pipeline, the memory preferably includes a correction factor.

FIGS. 5-7 illustrate a vortex-shedding body 63 of the process density meter 33 further including a total pressure manifold 115 positioned in the vortex-shedding body 63 and adjacent the upstream surface 81. The total pressure manifold 115 has a plurality of total pressure inlet channels 117 which are preferably coaxially aligned with the plurality of total pressure inlet ports 85 in the upstream surface 81, and a total pressure outlet channel 119 which is in fluid communication with the plurality of total pressure inlet channels 117 so that the fluid 41 when flowing through the pipeline 31 communicates through each of the total pressure inlet ports 85 to the total pressure outlet channel 119. The vortex-shedding body 63 also includes a static pressure manifold 121 positioned in the vortex-shedding body 63 and adjacent the downstream surface or surfaces 83 having the corresponding static pressure inlet ports 87. The static pressure manifold 121 has a plurality of static pressure inlet channels 123 aligned with the plurality of static pressure inlet ports 87 and a static pressure outlet channel 125 so that the fluid 41 when flowing through the pipeline 31 communicates through each of the static pressure inlet ports 87 to the static pressure outlet channel 125. In an alternative embodiment of the present invention, instead of the total pressure manifold and static pressure manifolds 115, 121, the vortex-shedding body 63 can have a central cavity (not shown) to house or support various alternative components of a differential pressure meter 89 (described later).

The process density meter 33 also includes a differential pressure measuring device such as a differential pressure meter 89. The differential pressure meter 89 is preferably positioned adjacent the vortex-shedding body 63. The differential pressure meter 89 includes a total pressure inlet 127 positioned to sense fluid pressure from the total pressure manifold outlet channel 119, and a static pressure inlet 129 positioned to sense fluid pressure from the static pressure manifold outlet channel 125. In an embodiment where the vortex-shedding body 63 has a central cavity (not shown) rather than a total pressure manifold 115 or static manifold 121, the differential pressure meter 89 includes a total pressure extension tube (not shown) and a static pressure extension tube (not shown), both having the plurality of inlet channels and ports which provide the functions of the above described total pressure and static pressure manifolds 115, 121.

FIGS. 10 and 11 illustrate that a differential pressure meter 89 also can include a differential pressure converter 131 positioned to receive fluid pressure from the total pressure inlet 127 and the static pressure inlet 129 to produce a differential pressure meter flow rate signal proportional to density of fluid 41 when flowing through the pipeline 31. Functionally, the total pressure inlet 127, through the upstream ports 85 of the vortex-shedding body, "sees" the total pressure of the fluid 41. This total pressure is the sum of the static pressure, the pressure a user would measure with a pressure gauge installed on the pipeline 31, plus the kinetic pressure of the flowing fluid 41, the result of the impact effect of the flowing fluid 41 on the upstream surface 81 of the vortex-shedding body 63. The static pressure inlet 129, through the downstream ports 87 of the vortex-shedding body 63, only "see" the static pressure. The calculation of the difference between the total pressure and the static pressure of the flowing fluid 41 results in the kinetic pressure of the flowing fluid 41, which is related to fluid density and velocity.

In a preferred configuration, the differential pressure meter 89 is positioned also to receive an ambient temperature signal and a static pressure signal. The ambient temperature signal can be either from an ambient temperature sensor 111 associated with the thermal flow meter 97 (described later) or the separate ambient temperature sensor 113. The static pressure signal can be either from the differential pressure meter 89, a tap in the static pressure inlet 129, or determined from a separate static pressure sensor (not shown). The ambient temperature signal and static pressure signal can be used by the differential pressure meter 89 to produce a temperature and pressure compensated differential pressure meter flow rate signal. If the differential pressure meter 89, however, is not so equipped to accept such inputs for compensating the differential pressure meter flow rate signal for pressure and temperature, a separate signal conditioner 133 (described later) can be used either on the differential pressure meter flow rate signal or on a later calculated density signal (described later).

The differential pressure flow meter 89, preferably in the form of an averaging pitot tube-type measuring device, can employ a multitude of methodologies as known by those skilled in the art to produce the differential pressure meter flow rate signal that is proportional to density of fluid when flowing through the pipeline. In a large number of averaging pitot tube differential pressure flow meters, the output of the meter is a signal proportional to the product of the density of the fluid and the square of the volumetric flow rate $\rho V^2$. In the preferred configuration, according to an embodiment of the present invention, however, the output of the averaging pitot tube differential pressure meter is in the form of either volumetric flow rate under standard conditions or pressure and temperature compensated volumetric flow rate. The following is an illustrative example for a calculation of the volumetric flow rate (gas-standard conditions) using an averaging pitot equation:

$$Q_{pitot} = C^1 \times \sqrt{h_w \times p_f},$$

where $C^1 = F_{na} \times K \times D^2 \times Y_a \times F_{pb} \times F_{tb} \times F_{tf} \times F_{Sg} \times F_{pv} \times F_{aa}$, and where $Q_{pitot}$ Standard Volumetric Flow Rate. This term is the flow rate of the fluid passing the vortex-shedding body expressed in standard volume units per unit of time. For this equation, the base pressure is 14.73 psia and the base temperature is 60° F.

$F_{na}$ Units Conversion Factor. This factor is used to convert the flow rate to the desired or wanted set of units, typically standard cubic feet per day.

K Flow Coefficient. This factor takes into account the diameter of the pipeline and is expressed as a function of the Reynolds number.

D Internal diameter of pipe, inches (mm).

$Y_a$ Expansion Factor. This factor has little effect on flow and thus, they can be estimated based on the typical gas that is used in the application, with very little error.

$F_{pb}$ Pressure Base Factor. This factor provides gas volumes at a pressure base of 14.73 psia. $F_{pb}$=14.73/base pressure, psia.

$F_{tb}$ Temperature Base Factor. This factor is calculated to give gas volumes at a base temperature of 60° F. and can be calculated as: $F_{tb}$=(base temperature (° F.)+460)/520.

$F_{tf}$ Flowing Temperature Factor. This factor corrects for tabular data taking at a gas temperature other than 60° F. $F_{tf}$=520/√(Flowing temperature (° F.)+460).

$F_{Sg}$ Specific Gravity Factor. This factor corrects the flow equation whenever the gas is not air. The factor can be calculated as: $F_{Sg} = \sqrt{1/SG}$.

SG Specific Gravity of Flowing Liquid. Ratio of the density of the flowing fluid to the density of water at 60° F.

$F_{pv}$ Supercompressibility Factor. This factor accounts for the deviation from the "ideal gas" laws and is typically determined through testing at expected pressure and temperature conditions, but can be estimated based on the typical gas used in the application, with very little error.

$F_{aa}$ Thermal Expansion Factor which corrects for the flowing area change of the pipe at the vortex-shedding body location due to temperature effects.

$h_w$ Differential (kinetic) pressure expressed as the height, in inches, of a water column at 68° F. at standard gravity ($g_0$=32.174 ft/sec$^2$=9.807 m/sec$^2$).

$P_f$ Flowing Pressure. This is the static pressure of the pipeline expressed in psia.

Figure 8:
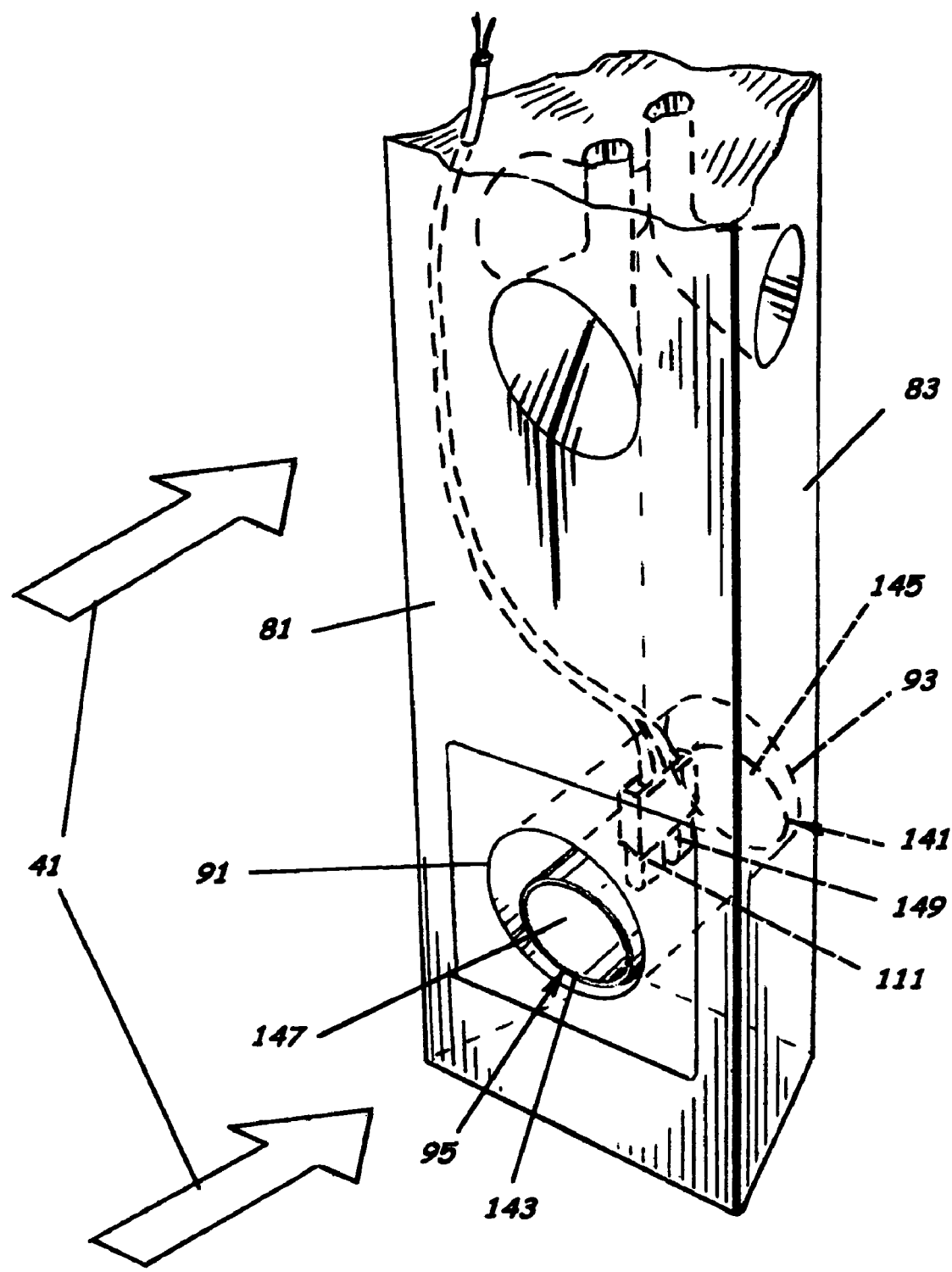
FIG. 8 is a partial perspective sectional view of a section of the vortex shedding body of FIG. 7 according to an embodiment of the present invention.

As perhaps best shown in FIGS. 7, 8, and 11, advantageously, in an embodiment of the present invention, a process density meter 33 can include a thermal flow measuring device, such as a thermal flow meter 97, appropriately positioned to produce a mass flow rate signal indicative of a mass flow rate of fluid 41 when flowing through the pipeline 31. The thermal flow meter 97 can have one or multiple thermal flow meter elements installed in, on, or next to the leading edge of the vortex-shedding body 63, but is preferably positioned within the vortex-shedding body 63 to minimize electrical wiring requirements.

More specifically, the thermal flow meter 97 preferably includes an immersion-type thermal flow probe 141 positioned to house a plurality of thermal sensors and positioned within the fluid passageway 95 extending between the thermal sensor inlet port 91 and thermal sensor outlet port 93 in the vortex-shedding body 63. Though other types of thermal flow detectors or sensors may be used and still be within the scope of the present invention, the immersion-type probes are simple, rugged, insensitive to particulate matter within the flowing fluid, and easily cleaned. The thermal flow probe 141 typically has a thermal sensor inlet 143 positioned in fluid communication with the thermal sensor inlet port 91 in the upstream surface 81 of the vortex-shedding body 63, and a thermal sensor outlet 145 positioned in fluid communication with the thermal sensor outlet port 93 in at least one of the downstream surfaces 83 of the vortex-shedding body 63. A thermal probe channel 147 extends between the thermal sensor inlet 143 and the thermal sensor outlet 145 so that a portion of fluid 41 when flowing through the thermal sensor inlet port 91 passes into and through the thermal sensor inlet 143, and so that the portion of fluid 41 passing into and through the thermal sensor inlet 143 passes out of the thermal sensor outlet 145 and out of the thermal sensor outlet port 93 (FIGS. 3 and 4). As stated above, although the thermal flow probe 141 is described as positioned within the vortex-shedding body 63, the thermal flow probe 141 can be alternatively positioned on or next to the vortex-shedding body 63 provided the thermal flow probe 141 is able to receive or "see" the flowing fluid 41 and the flow through the thermal flow probe 141 is either not obstructed or the thermal flow meter 97 compensates for the disturbed flow resulting from the obstruction.

An ambient temperature sensor 111 is preferably positioned within the thermal probe channel 147 to detect ambient temperature of the portion of fluid 41 flowing between the thermal sensor inlet 143 and thermal sensor outlet 145. A thermal flow detection sensor 149 is also preferably positioned within the thermal probe channel 147 to sense an amount of thermal energy removed by the portion of fluid 41 flowing between the thermal sensor inlet 143 and the thermal sensor outlet 145. In the selected configuration of the thermal flow meter 97 described with respect to the figures, the thermal flow meter 97 further includes a thermal flow meter mass flow signal calculator 151 responsive to the ambient temperature sensor 111 and the thermal flow detection sensor 149 to produce either a voltage or a current required to maintain a constant temperature differential between the ambient temperature sensor 111 and the thermal flow detection sensor 149. This constant current or voltage is used to calculate the mass flow rate signal of the thermal flow meter 97. If the fluid flow is obstructed when flowing through the thermal sensors of the thermal flow meter 97, the mass flow signal calculator 151 of the thermal flow meter 97 can include a thermal mass flow signal compensator 153 to compensate for an error induced by the obstructed flow.

FIG. 10 illustrates that a process density meter 33 can further include a fluid characteristic determiner 161 positioned in communication with the vortex meter 65, the differential pressure meter 89, and the thermal flow meter 97, to process sensed signals therefrom. The fluid characteristic determiner 161 includes a fluid density calculator 163 and can include a fluid mass flow rate calculator 165. In the preferred configuration, the fluid density calculator 163 is responsive to the volumetric flow rate signal $Q_{vortex}$ received from the vortex meter 65 and the differential pressure meter flow rate signal $Q_{pitot}$ received from the differential pressure meter 89 and is positioned to calculate a density signal indicative of flowing fluid density Density$_{flowing}$.

In the illustrative example for a calculation of the volumetric flow rate $Q_{pitot}$ using an averaging pitot equation, described above, the $F_g$ factor ($F_g = (1/SG)^{1/2}$) of the equation is the influence of gas specific gravity (SG) on the averaging pitot tube, and this is what provides the ability to obtain density from the averaging pitot tube flow rate calculation. For example, the $SG_{base}$ used in the equation in the illustrative example is that of the flowing gas. When the specific gravity of the flowing gas changes, the flow calculation $Q_{pitot}$ must be compensated by multiplying it by the square root of the ratio of the base specific gravity divided by the true specific gravity.

$$Q_{true} = Q_{pitot} * (SG_{base}/SG_{flowing})^{1/2}.$$

Noting that the flow rate from the vortex meter is NOT influenced by the specific gravity of the flowing gas, the volumetric flow rate $Q_{vortex}$ from the vortex meter is equivalent to true volumetric flow rate:

$$Q_{vortex} = Q_{true} = Q_{pitot} * (SG_{base}/SG_{flowing})^{1/2}.$$

By compensating the $Q_{pitot}$ for changes in SG of the flowing gas, and manipulating the equations, the true (flowing gas) specific gravity can be determined:

$$SG_{flowing} = SG_{base} * (Q_{pitot}/Q_{vortex})^2.$$

Correspondingly, density can be calculated as a factor true (flowing gas) specific gravity and base density:

$$\text{Density}_{flowing} = \text{Density}_{base} * (SG_{flowing}/SG_{base}).$$

Similar to the fluid density calculator 163, in an embodiment of the present invention, the fluid mass flow rate calculator 165 is responsive to the volumetric flow rate signal $Q_{vortex}$ received from the vortex meter 65 and the differential pressure meter flow rate signal $Q_{pitot}$ received from the differential pressure meter 89 and is positioned to calculate a mass flow rate signal indicative of flowing fluid mass flow rate $Q_{massflow}$. After performing calculations similar to those above, the mass flow rate $Q_{massflow}$ is then calculated as a function of the product of the flowing fluid density Density$_{flowing}$ and the volumetric flow rate $Q_{vortex}$:

$$Q_{massflow} = \text{Density}_{flowing} * Q_{vortex}.$$

In an alternative configuration, the mass flow rate calculator 165 is instead responsive to the flowing fluid density signal Density$_{flowing}$ from the fluid density calculator 163 and the volumetric flow rate signal $Q_{vortex}$ from the vortex meter to calculate mass flow $Q_{massflow}$.

FIGS. 7 and 11 illustrate that where the process density meter 33 includes the vortex meter 65, the differential pressure meter 89, and a third meter to measure and output a mass flow rate signal, such as the thermal flow meter 97, described above, the process density meter 33 can also include a verifier 171 responsive to the density signal and the mass flow rate signal from the fluid characteristic determiner 161 to verify the accuracy of the density signal and mass flow rate signal from the fluid characteristic determiner 161. To perform the density comparison, the verifier 171 has its own fluid density calculator 173 responsive to the mass flow rate signal from the thermal flow meter 97 and the volumetric flow rate signal from the vortex meter 65 to calculate a verification density signal to be used to compare with the density signal from the fluid density calculator 163 of the fluid characteristic determiner 161. If both density signals are within a minimum tolerance of each other, such as 4%, the verifier 171 can output a signal indicating a minimum accuracy of the process density meter 33 has been met.

To perform the density comparison, the verifier 171 also has a comparator 175 that is responsive to the density signal from the fluid characteristic determiner 161 and is positioned to receive the density signal from the fluid density calculator 173 of the verifier 171 to compare the density signal from the fluid characteristic determiner 161 with the density signal from the fluid density calculator 173 of the verifier 171 to verify reliability of the density signal from the fluid characteristic determiner 161, to output a density verification signal indicating verified density, and to thereby determine the accuracy of the density signal from the fluid characteristic determiner 161. To perform the mass flow rate comparison, the comparator 175 of the verifier 171 is responsive to the mass flow rate signal from the fluid characteristic determiner 161 and is positioned to receive the mass flow rate $Q_{thermal}$ from the thermal flow meter 97 to compare the mass flow rate signal $Q_{massflow}$ from the fluid characteristic determiner 161 with the mass flow rate signal from the thermal flow meter 97 to verify reliability of the mass flow rate from the fluid characteristic determiner 161, to output a mass flow rate verification signal indicating verified mass flow rate, and to thereby determine the accuracy of the mass flow rate signal from the fluid characteristic determiner 161.

Note, the volumetric flow rate calculator 105, differential pressure converter 131, mass flow signal calculator 151, mass flow signal compensator 153, fluid density calculator 163, fluid characteristic determiner 161, mass flow rate calculator 165, verifier 171, and signal conditioner 133 can be implemented in either hardware or software/program product alone or in combination. The software/program product can be in the form of microcode, programs, routines, and symbolic languages that provide a specific set for sets of ordered operations that control the functioning of the hardware and direct its operation, as known and understood by those skilled in the art. Note also, the fluid characteristic determiner 161 can be implemented in the form of a computer/processor, and, though illustrated separately, the signal conditioner 133 and the verifier 171 along with the volumetric flow rate calculator 105, differential pressure converter 131, mass flow signal calculator 151, mass flow signal compensator 153, fluid density calculator 163, and mass flow rate calculator 165, and the functions associated with the fluid characteristic determiner 161 can be processed by such computer/processor. Further, the software/program product can be separately stored on a storage media readable by, for example, such computer/processor or by separate independent processors.

In an embodiment of the present invention, the process density meter 97 can include a signal conditioner 133. As stated above, the signal conditioner 133 can be used either to pressure and temperature compensate the differential pressure meter flow rate signal from the differential pressure meter 89 or pressure and temperature compensate the fluid density signals from the fluid characteristic determiner 161 where the differential pressure meter selected is not capable of independently applying pressure and temperature compensation directly to its output signal. For example, as best shown in FIG. 11, when positioned to compensate the output signals of the fluid characteristic determiner 161, the signal conditioner 133 is responsive to the density signal from the fluid characteristic determiner 161 and is positioned to receive a temperature signal from the ambient temperature sensor 111 of the thermal flow meter 97 or separate ambient temperature sensor 113 and a static pressure signal from the differential pressure meter 89. The signal conditioner 133 conditions the density signal of the fluid density calculator 163 of the fluid characteristic determiner 161 to form a temperature and pressure compensated density signal. Where the process density meter 33 is also configured with a verifier 171, the comparator 175 of the verifier 171 receives the density signal from the signal conditioner 133 instead of directly from the fluid characteristic determiner 161, as described above, otherwise all calculations are the same.

As best shown in FIGS. 1, 2, 10-11, a system 30 for measuring fluid flow characteristics in a pipeline, or alternatively the process density meter 33, itself, also includes a fluid characteristic display 35 positioned external to the fluid passageway 37 of the pipeline 31. The fluid characteristic display 35 is in electrical communication with other process density meter components and is typically located remote from the process density meter sensors. The fluid characteristic display 35 is positioned to receive the volumetric flow rate signal, the density signal, and the mass flow rate signal to display volumetric flow rate 182, flowing fluid density 183, and mass flow rate 184 of the flowing fluid. The volumetric flow rate is preferably received from the vortex meter 65. The density signal and mass flow rate signals are typically from the fluid characteristic determiner 161, however, if a signal conditioner 133 is utilized and implemented to condition the signals from the fluid characteristic determiner 161, the density signal can instead be from the signal conditioner 133. Also, where the process density meter 33 is configured with a verifier 171, the fluid characteristic display 35 further can display density verified and mass flow rate verified indications 185, 186.

Figure 9:
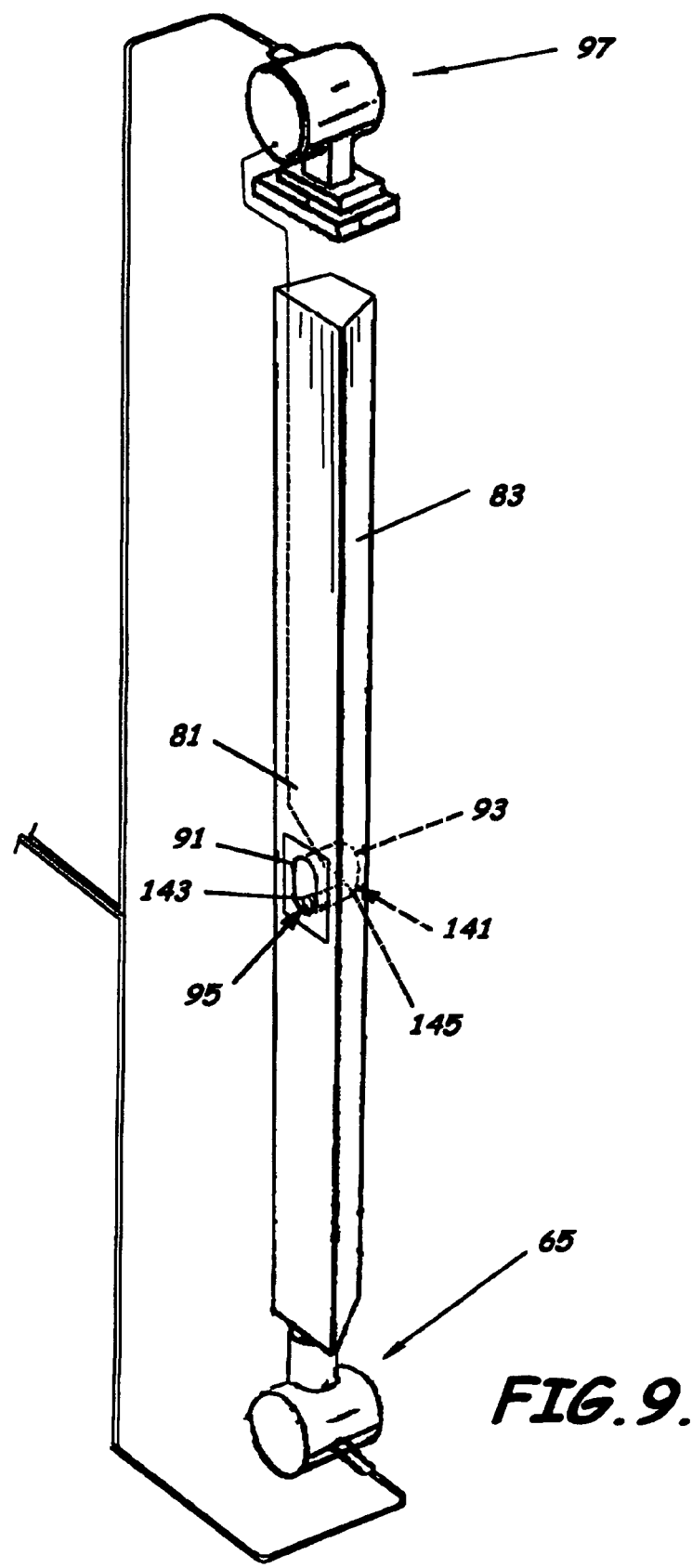
FIG. 9 is a partial perspective sectional view of another embodiment of the process density meter of according to another embodiment of the present invention.
Figure 12:
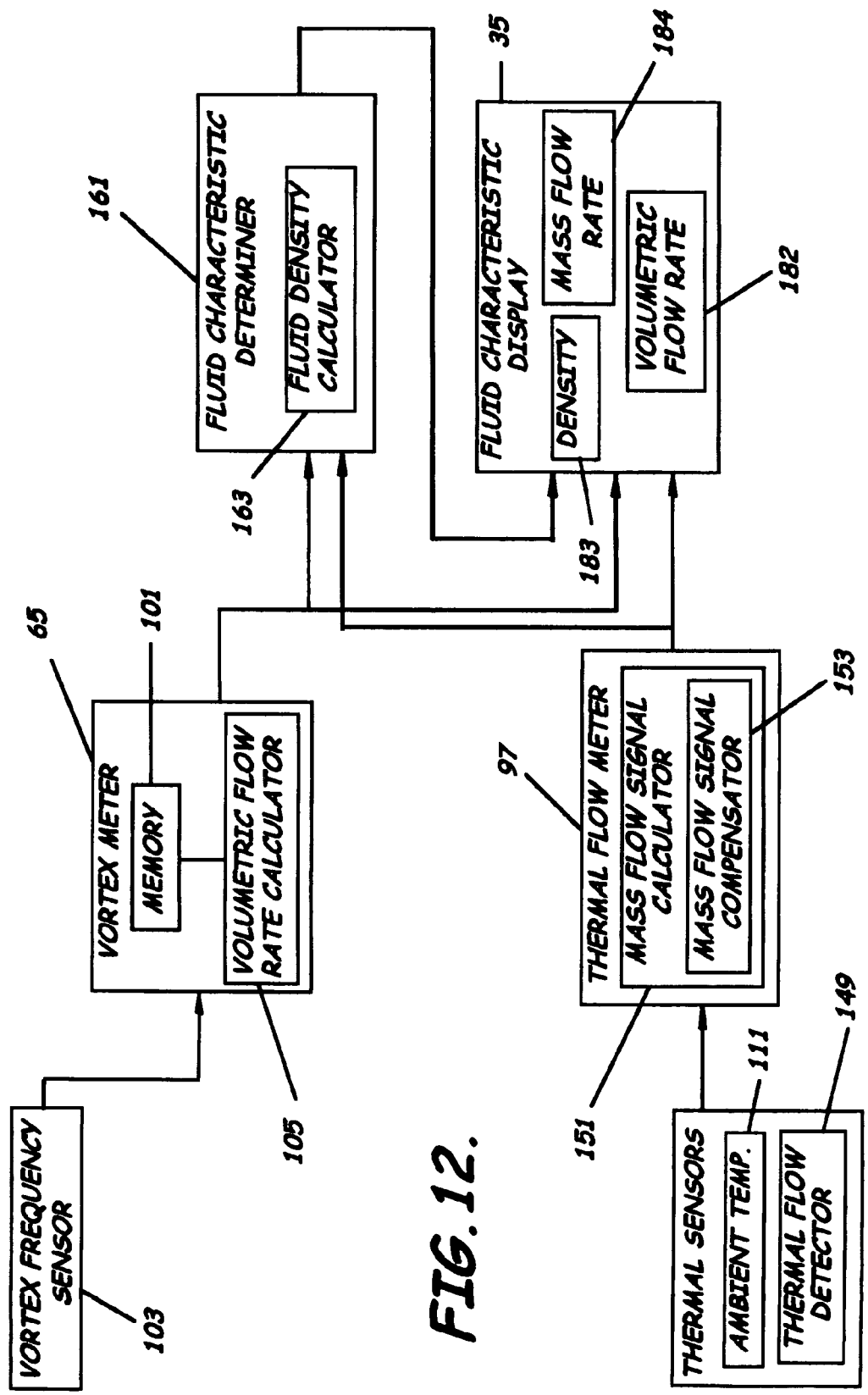
FIG. 12 is a functional block diagram illustrating a basic structure of a process density meter circuit of FIG. 9 according to an embodiment of the present invention.

Advantageously, as perhaps best shown in FIGS. 9 and 12, another embodiment of the present invention also includes a process density meter 33 for measuring fluid flow characteristics in a pipeline 31 including a fluid passageway 37 having a longitudinal axis 39 to transport fluid 41 therethrough and positioned at least partially within the pipeline 31. The process density meter 33 generally includes a vortex-shedding measuring device and associated equipment, such as a vortex meter 65, a mass flow rate measuring device and associated equipment, such as a thermal flow meter 97, a fluid characteristic determiner 161, and a fluid characteristic display 35 which is located external to the fluid passageway 37 of the pipeline 31 and in communication with the vortex meter 65 and the fluid characteristic determiner 161, and positioned to receive a volumetric flow rate signal from the vortex meter 65, a mass flow rate from the thermal flow meter 97, and a fluid density signal from the fluid characteristic determiner 161 to display volumetric flow rate, density, and mass flow rate of the flowing fluid to a user thereof.

As with the previous described embodiments, in the typical configuration, the bulk of the electronics, other than sensors, are located external to the pipeline 31, and the sensors and related equipment are located within the confines of the pipeline 31. The process density meter 33 can include a process density meter housing to house the sensors and related equipment and to support a vortex-shedding body 63 of the vortex meter 65 within the flowing fluid 41 of the pipeline 31. In one configuration, the process density meter housing 61 is positioned coaxially between a pair of upstream and downstream sections 43, 45, of the pipeline 31 (FIG. 2). The process density meter housing 61 is adapted to connect between the upstream and downstream sections 43, 45, of the pipeline 31 through use of a connection assembly as known and understood by those skilled in the art. The process density meter housing 61 is preferably sized to match a section of the pipeline 31 such that the process density meter housing 61 has an inner diameter 75 substantially the same as the predetermined inner diameter 55 of the pipeline 31. In a second configuration, as best shown in FIG. 3, the process density meter housing 61' can be instead sized to fit within a section of the pipeline 31. In this configuration, the outer diameter 77 of the process density meter housing 61' is preferably substantially the same diameter as the predetermined inner diameter 55 of the pipeline 31. In a third configuration, as best shown in FIG. 4, instead of supplying a separate process density meter housing, the sensors and associated equipment can be positioned and supported within a section of the pipeline 31. In this configuration, the pipeline 31 functions as a process density meter housing 61".

FIGS. 4, 9 and 12 illustrate a process density meter 33 including a vortex-shedding body 63 positioned within the pipeline 31. The vortex-shedding body 63 is preferably in the form of a three-dimensional bluff body having an upstream side 81 and a plurality of downstream sides 83. The vortex-shedding body 63 is preferably adapted to connect to the pipeline 31 or pipeline housing 61 on opposite sides within the fluid passageway 41 of the pipeline 31, as perhaps best shown in FIG. 4, but can be less than the diameter of the pipeline 31 or pipeline housing 61 and still be within the scope of the present invention.

FIGS. 4 and 9 illustrate a vortex-shedding body 63 including an upstream surface 81 positioned transverse to the longitudinal axis 39 of the pipeline 31 which preferably has or contains a thermal sensor inlet port 91. The vortex-shedding body 63 also includes a plurality of downstream surfaces 83, at least one of which preferably has or contains a thermal sensor outlet port 93. A fluid passageway 95 extends between the thermal sensor inlet port 91 and the thermal sensor outlet port 93 so that fluid flowing through the pipeline passes therethrough for use with a thermal flow sensing device such as the thermal flow meter 97 (described later).

FIG. 12 illustrates that the process density meter 33 can also include a vortex measuring device such as a vortex meter 65. The vortex meter 65 measures the frequency of vortices shed from the vortex-shedding body 63 to produce a signal indicative of volumetric fluid flow rate $Q_{vortex}$ within the pipeline 31. The vortex meter 65, optionally positioned adjacent the vortex-shedding body, includes a memory 101, a vortex frequency sensor 103, and a volumetric flow rate calculator 105. The memory 101 stores pipeline volume data for use by the volumetric flow rate calculator 105. The pipeline volume data generally includes the inner diameter 55 of the pipeline 31 along with other data as known to those skilled in the art necessary to determine cross-sectional area of the inner dimensions of the pipeline 31. The vortex frequency sensor 103, senses the frequency of vortices shed by the vortex-shedding body 63 to thereby produce a fluid flow rate signal responsive to the frequency of vortices shed by the vortex-shedding body 63. As stated with regard to the previous embodiments, the vortex frequency sensor 103 is preferably in the form of a strain gauge or pressure transducer positioned in the vortex-shedding body 63 or process density meter housing 61 but can embody other forms and be positioned at other locations adjacent the vortex-shedding body 63 and still be within the scope of the present invention. The volumetric flow rate calculator 105, positioned to receive the pipeline volume data stored in the memory 101 and the flow rate signal from the vortex frequency sensor 103, calculates a volumetric flow rate signal indicative of volumetric flow rate of fluid 41 when flowing through the pipeline 31. In another configuration, the volumetric flow rate calculator 105 of the vortex meter 65 further is positioned to receive an ambient temperature signal and a static pressure signal. The ambient temperature signal can be either from an ambient temperature sensor 111 associated with a thermal flow meter 97 or a separate ambient temperature sensor 113 (FIG. 4). The static pressure signal can be from a separate static pressure sensor (not shown). The ambient temperature and static pressure can be used by the vortex meter to produce a temperature and pressure compensated volumetric flow rate signal by compensating the flow rate signal corresponding to the frequency of the vortices shed by the vortex-shedding body 63 for the temperature and pressure experienced by the vortex frequency sensor 103. In both configurations, a volumetric flow rate $Q_{vortex}$ can be calculated using the formula:

$$Q_{vortex} = A \times v,$$

where A is the cross-sectional area of the portion of pipeline where flow rate is measured and v is the fluid flow rate. Additionally, if the inner dimension 75 of the pipeline housing 61 is not substantially the same as the inner dimension 55 of the pipeline, the memory 101 preferably includes a correction factor.

The process density meter 33 advantageously includes a thermal mass flow detection device such as a thermal flow meter 97. The thermal flow meter 97 is appropriately positioned to produce a mass flow rate signal $Q_{thermal}$ indicative of a mass flow rate of fluid 41 when flowing through the pipeline 31. The thermal flow meter 97 can have one or multiple thermal flow meter elements installed in, on, or next to the leading edge of the vortex shedding meter body 63, but is preferably positioned within the vortex-shedding body 63 to minimize electrical wiring requirements and to reduce the complexity of the process density meter 33.

The thermal flow meter 97 preferably includes an immersion-type thermal flow probe 141 positioned to house a plurality of thermal sensors and positioned within the fluid passageway 95 extending between the thermal sensor inlet port 91 and thermal sensor outlet port 93 in the vortex-shedding body 63. The thermal flow probe 141 typically has a thermal sensor inlet 143 positioned in fluid communication with the thermal sensor inlet port 91 in the upstream surface 81 of the vortex-shedding body 63 to allow a portion of fluid flowing through the fluid passageway 95 to enter the thermal flow probe 141, and a thermal sensor outlet 145 positioned in fluid communication with the thermal sensor outlet port 93 in at least one of the downstream surfaces 83 of the vortex-shedding body 63 to allow the portion of fluid to exit the thermal flow probe 141. A thermal probe channel 147 extends between the thermal sensor inlet 143 and the thermal sensor outlet 145 so that a portion of fluid 41 when flowing through the thermal sensor inlet port 91 passes into and through the thermal sensor inlet 143, and so that the portion of fluid 41 passing into and through the thermal sensor inlet 143 passes out of the thermal sensor outlet 145 and out of the thermal sensor outlet port 93 (FIG. 4). As stated above, although the thermal flow probe 141 is shown in the figures and described as positioned within the vortex-shedding body 63, the thermal flow probe 141 can be alternatively positioned on or next to the vortex-shedding body 63 provided the thermal flow probe 141 is able to receive or "see" the flowing fluid 41 and the flow through the thermal flow probe 141 is either not obstructed or the thermal flow meter 97 compensates for the disturbed flow resulting from the obstruction.

An ambient temperature sensor 111 is preferably positioned within the thermal probe channel 147 to detect the ambient temperature of the portion of fluid 41 flowing between the thermal sensor inlet 143 and thermal sensor outlet 145. A thermal flow detection sensor 149 is also preferably positioned within the thermal probe channel 147 to sense an amount of thermal energy removed by the portion of fluid 41 flowing between the thermal sensor inlet 143 and the thermal sensor outlet 145. In the selected configuration of the thermal flow meter 97 described with respect to the figures, the thermal flow meter 97 includes a thermal flow meter mass flow signal calculator 151 responsive to the ambient temperature sensor 111 and the thermal flow detection sensor 149 to produce either a voltage or a current required to maintain a constant temperature differential between the ambient temperature sensor 111 and the thermal flow detection sensor 149. This constant current or voltage is used to calculate the mass flow rate signal $Q_{thermal}$ of the thermal flow meter 97. If the fluid flow is obstructed when flowing through the thermal sensors of the thermal flow meter 97, for example, where the thermal probe channel 147 is not parallel to the longitudinal axis 39 of the pipeline 31 due to non-symmetric positioning of the upstream surface 81 of the vortex-shedding body 63 or non-symmetric positioning of the thermal flow probe 141 or channel 147, the mass flow signal calculator 151 of the thermal flow meter 97 can include a thermal mass flow signal compensator 153 to compensate for an error induced by the obstructed flow.

The fluid characteristic determiner 161 includes the primary calculator assembly of the process density meter 33. The fluid characteristic determiner 161 is positioned in communication with the vortex meter 65 and the thermal flow meter 97, to process sensed signals therefrom. The fluid characteristic determiner 161 includes a fluid density calculator 163. Although the fluid characteristic determiner may include a mass flow calculator, the mass flow rate calculator is not required according to this embodiment of the present invention as the thermal flow meter 97 directly produces a signal $Q_{thermal}$ indicative of a mass flow rate of fluid 41 when flowing through the pipeline 31. The fluid density calculator 163 is responsive to the volumetric flow rate signal $Q_{vortex}$ received from the vortex meter 65 and the thermal flow meter mass flow rate signal $Q_{thermal}$ received from the mass flow rate meter 97 and is positioned to calculate a density signal indicative of flowing fluid density Density$_{flowing}$, where:

$$\text{Density}_{flowing} = Q_{thermal}/Q_{vortex}.$$

FIG. 12 illustrates a fluid characteristic display 35 positioned external to the fluid passageway 37 the pipeline 31 of the process density meter 33 (FIG. 2) in communication with other components of the process density meter 33 and typically positioned remote from the process density meter sensors. The fluid characteristic display 35 is positioned to receive the volumetric flow rate signal, the density signal, and the second mass flow rate signal to display volumetric flow rate 182, flowing fluid density 183, and mass flow rate 184 of the flowing fluid 41. The volumetric flow rate is preferably received directly from the vortex meter 65. The density signal is received from the fluid characteristic determiner 161, and the mass flow rate signal is preferably directly from the thermal flow meter 97, though other methodologies of establishing a signal connection are within the scope of the present invention.

An embodiment of the present invention also advantageously provides a method for measuring flowing fluid characteristics in a pipeline using a process density meter having at least portions thereof positioned within a fluid passageway of the pipeline. Generally, the method includes positioning a vortex-shedding (bluff) body within a pipeline, measuring the frequency of the vortices shed from the vortex-shedding body, determining volumetric flow rate, measuring the differential between the pressure experienced on the flow side of the vortex-shedding body and the static pressure of the fluid in the pipeline, measuring the static pressure and ambient temperature of the fluid in the pipeline, determining density and mass flow rate, and outputting density, mass flow rate, and volumetric flow rate for display.

Figure 13A:
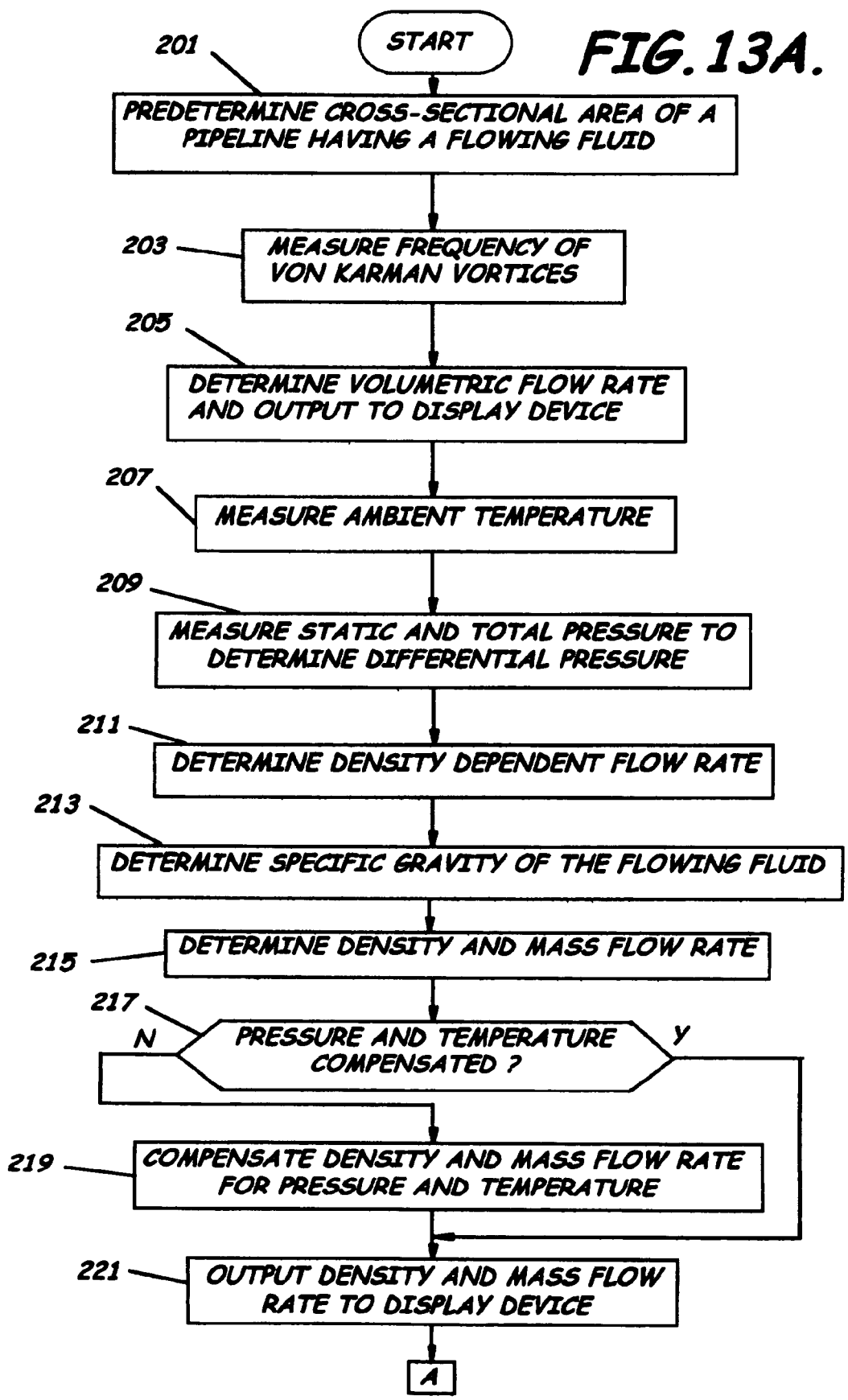
FIG. 13 is a flowchart of a method for measuring flowing fluid characteristics in a pipeline according to an embodiment of the present invention.

More specifically, as perhaps best shown in FIG. 13, a user predetermines a cross-sectional area of a pipeline 31 having a flowing fluid 41 (block 201). The user installs the vortex-shedding body 63. The installation can be accomplished by individually installing the vortex-shedding body 63 within an existing piece of pipeline 31 (FIG. 4), or by installing the vortex-shedding body 63 within a housing 61 which can be positioned coaxially between an upstream and a downstream section 43, 45, of the pipeline 31 (FIG. 2) or within a pipeline interior passageway 37 (FIG. 3). The vortex-shedding body 63 is generally positioned across the inner diameter 55 of the pipeline, transverse to the direction of a flowing fluid 41. The upstream surface 81 of the vortex-shedding body 63 is preferably placed perpendicular to the direction of the flowing fluid 41. The vortex-shedding body 63 causes the generation of Von Karman vortices when fluid 41 is flowing within the pipeline 31. The vortex-shedding body 63 also includes upstream ports 85 that are affected by fluid 41 flowing within the pipeline 31 having a total pressure equivalent to the sum of the kinetic and static pressures of the flowing fluid 41. The vortex-shedding body 63 further includes downstream ports 87 which are affected by fluid 41 flowing within the pipeline 31 having only static pressure, and a pair of manifolds 115, 121, within the vortex-shedding body 63 to individually channel fluid having total pressure separate from fluid having only static pressure.

The user also installs a vortex frequency detection device 103, part of a vortex (shedding) meter 65, on, and, or within either the vortex-shedding body 63, the process density meter housing 61, or the pipeline 31, in the vicinity of the vortex-shedding body 63. The vortex frequency sensor 103, as described above, typically takes the form of a strain-gauge, a pressure transducer, or an acoustic sensor. As fluid flows 41 through the pipeline 31, the bluff body (vortex-shedding) 63 causes vortices to be shed. The vortex meter 65 measures (block 203) the frequency of Von Karman vortices shed by a vortex-shedding body 63. The vortex meter 65 then outputs a respective true vortex meter flowing fluid flow rate signal. The vortex meter can also determine and output volumetric flow rate (block 205) from the true flowing fluid rate measured by the vortex frequency sensor in conjunction with predetermined pipeline volumetric data, generally stored in the memory of the vortex meter. The vortex meter 65 typically determines volumetric flow rate by calculating the product of the fluid flow rate as determined from the vortex frequency sensor 103 and the cross-sectional area of the column fluid 41 flowing within the pipeline 31. Other methodologies of determining the pipeline flowing fluid rate and correspondingly the volumetric flow rate through use of a vortex-shedding body, known and understood by those skilled in the art are, of course, within the scope of the present invention.

The user installs a differential pressure meter 89, preferably in the form of an averaging pitot tube, to interface with the vortex-shedding body 63. The user also installs either a thermal flow probe 141 having ambient temperature sensor 111 or a separate ambient temperature sensor 113 positioned to be able to sample the temperature of the flowing fluid 41 within the pipeline 31, generally unaffected by other components of the present invention. The ambient temperature sensor 113 is typically in the form of a thermistor but can be another type of sensor known and understood by those skilled in the art. The ambient temperature of the flowing fluid 41 and static pressure of the flowing fluid 41 is measured (block 207). The differential pressure meter 89 measures the total pressure of the flowing fluid 41 on the vortex-shedding body 63 and the static pressure of the flowing fluid and can determine the differential pressure (block 209) between a total and static pressures. The differential pressure meter further determines (block 211) and outputs a density dependent flow rate signal that is typically proportional to a volumetric flow rate but can be proportional to other density and flow rate dependent values. In some configurations, the differential pressure meter output signal can be corrected for temperature and pressure by the differential pressure meter.

A true flowing fluid specific gravity can be determined (block 213) from the predetermined base specific gravity of the fluid, the vortex meter flowing fluid flow rate, and density dependent differential pressure meter flow rate. Density of the flowing fluid 41 can correspondingly be determined (block 215) from the flowing fluid specific gravity and base density by a fluid characteristic determiner 161 having a fluid density calculator 163. Mass flow can also be calculated from the flowing fluid density calculated by the fluid characteristic determiner 161 and volumetric flow rate from the vortex meter 65.

Where the configuration selected for the differential pressure meter 89 does not provide for pressure and temperature compensation (block 217), the density and mass flow calculation can be inaccurate. A signal conditioner 133 can determine density corrected for pressure and temperature (block 219) from the static pressure of the differential pressure meter 89 and ambient temperature of the independent ambient temperature sensor 113 or ambient temperature sensor 111 of the thermal flow meter 97, if so configured. In either configuration, density and mass flow rate, along with volumetric flow rate from the flow meter, are output (block 221) to a fluid characteristic display 35 in a manner known and understood by those skilled in the art.

In an embodiment of the present invention the user can install a thermal flow meter 97 or similar device adjacent the vortex-shedding body 63. If so installed (block 223), a mass flow meter can be used to verify the density and mass flow rate calculated from the differential pressure meter flow rate signal. The mass flow meter is typically in the form of a thermal flow meter 97 which measures a thermal energy change (block 225) proportional to the mass of fluid 41 interfacing with a thermal flow detector 149, and outputs a signal indicative of mass flow rate independent of density. The mass flow rate can be determined (block 227) directly from the mass flow meter 97. A verifier 171 having its own fluid density calculator 173 can determine a verification density (block 229) from the mass flow rate signal of the thermal flow meter 97 in conjunction with the volumetric flow rate signal from the vortex meter 65. The verifier 171, also having a comparator 175, can compare (block 231) the pressure and temperature compensated density signal from either a fluid characteristic determiner 161 or signal conditioner 133, depending upon the selected configuration, with the density signal from the fluid density calculator 173 of the verifier 171 in order to verify reliability of the density determined from the differential pressure meter flow rate signal. If the density signal is within a preselected tolerance (block 233), 4% for example, the verifier 171 can output (block 235) a density verified signal to the fluid characteristic display 35. The comparator 175 can also compare (block 237) the mass flow signal from the fluid characteristic determiner 161 with the mass flow rate signal from the thermal flow meter 97 in order to verify reliability of the mass flow rate determined from the differential pressure meter flow rate signal is within preselected tolerance (block 239), 4% for example. If so, the verifier can output (block 241) a mass flow rate verified signal to the fluid characteristic display 35.

Figure 14:
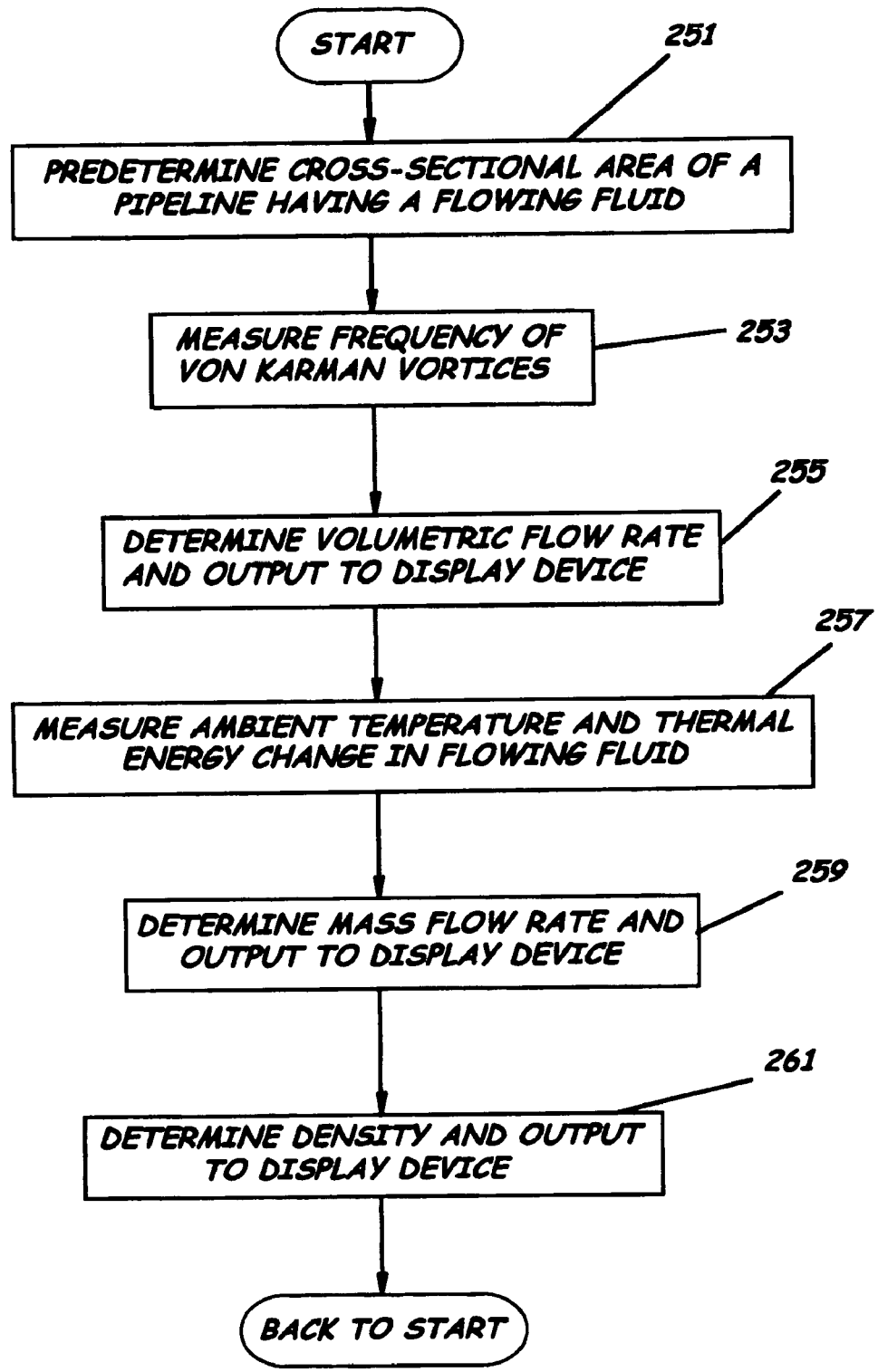
FIG. 14 is a flowchart of a method for measuring flowing fluid characteristics in a pipeline according to another embodiment of the present invention.

Another embodiment of the present invention, as perhaps best shown in FIG. 14, includes a method for measuring flowing fluid characteristics in a pipeline using a process density meter having at least portions thereof positioned within a fluid passageway of the pipeline. As with the previous embodiments, the user predetermines a cross-sectional area of a pipeline 31 having a flowing fluid 41 (block 251). The user also installs the vortex-shedding (bluff) body 63. The installation can be accomplished by individually installing the vortex-shedding body 63 within an existing piece of pipeline 31 (FIG. 4), or by installing the vortex-shedding body 63 within a housing 61 which can be positioned coaxially between an upstream and a downstream section 43, 45, of pipeline 31 (FIG. 2) or within a pipeline interior passageway 37 (FIG. 3). The vortex-shedding body 63 is generally positioned across the inner diameter 55 of the pipeline 31, transverse to the direction of a flowing fluid 41. The vortex-shedding body 63 causes the generation of Von Karman vortices which can be easily measured when fluid 41 is flowing within the pipeline 31.

The user also installs a vortex frequency detection device or sensor 103, part of a vortex meter 65, either in the vortex-shedding body 63, the process density meter housing 61, or in a position on, in, or within the pipeline 31 in the vicinity of the vortex-shedding body 63. As fluid 41 flows through the pipeline 31, the vortex-shedding body 63 causes vortices to be shed. The vortex meter 65 measures the frequency of Von Karman vortices (block 253) shed by the vortex-shedding body 63. The vortex meter 65 then determines (block 255) volumetric flow rate of the flowing fluid 41 from the flowing fluid flow rate measured by the vortex frequency sensor 103 and predetermined pipeline volumetric data, generally stored in a memory 101 of the vortex meter 65, and outputs a respective vortex meter flowing fluid flow rate signal for display. The vortex meter 65 typically determines volumetric flow rate by calculating the product of the fluid flow rate as determined from the vortex frequency sensor 103 and the cross-sectional area of the column of fluid 41 flowing within the pipeline 31.

The user also installs a thermal flow meter 97 or similar device adjacent the vortex-shedding body 63. The thermal flow meter 97 includes thermal sensors to measure ambient temperature and a thermal energy change in the flowing fluid 41 (block 257) from which the thermal flow meter can determine mass flow rate and output a signal indicative of mass flow rate (block 259) proportional to fluid density. A fluid characteristic determiner 161 having a fluid density calculator 163 can determine density (block 261) from the volumetric flow rate signal from the vortex meter 65, and mass flow rate signal from the thermal flow meter 97. All three fluid characteristic measurements, density, mass flow rate, and volumetric flow rate can be translated to the user through the fluid characteristic display 35 or other methodology as known and understood by those skilled in the art.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read only memories (ROMs) or erasable, electrically programmable read only memories (EEPROMs), recordable type media such as floppy disks, hard disk drives, CD-ROMs, CD-R/RWs, DVD-ROMs, DVD-RAMs, DVD-R/RWs, DVD+R/RWs, and flash drives, and transmission type media such as digital and analog communication links.

Embodiments of the present invention include a computer readable medium that is readable by a computer for measuring fluid flow characteristics in a pipeline. For example, according to an embodiment of the present invention, a computer readable medium can include a set of instructions that, when executed by a computer, cause the computer to perform the operation of calculating a density indicative of flowing fluid density and a mass flow rate indicative of flowing fluid mass flow rate, responsive to a received/measured volumetric flow rate and a received/measured differential pressure meter flow rate signal. The volumetric flow rate of fluid flowing in the pipeline 31, for example, can be received or measured from a vortex meter 65 positioned adjacent a vortex shedding bluff body 63 positioned in the pipeline 31. The vortex shedding bluff body 63 can have an upstream surface 81 including at least one total pressure inlet port 85 and a downstream surface 83 having at least one static pressure inlet port 87. The differential pressure meter flow rate signal for the flowing fluid, for example, can be received or measured from a differential pressure meter 89 positioned adjacent the vortex shedding bluff body 63. According to an embodiment of the present invention, the density can be determined by first determining the specific gravity of the flowing fluid from the volumetric flow rate and the differential pressure meter flow rate, as described previously.

The instructions can also include those to perform the operations of conditioning the density to form a temperature and pressure compensated density, responsive to a received or measured ambient temperature and static pressure. The ambient temperature, for example, can be received or measured from an ambient temperature sensor, e.g., sensor 111, electrically connected to a thermal flow meter 97, or sensor 113, positioned adjacent the vortex shedding bluff body 63. The static pressure, for example, can be received from or through the differential pressure meter 89. The instructions can also include those to perform the operations of providing data to display the volumetric flow rate 182, the conditioned density 183, and the conditioned mass flow rate 184, in their respective display fields.

The instructions can include those to perform the operation of determining density from a mass flow rate using, for example, a mass flow rate meter, e.g. thermal flow meter 97, and a volumetric flow rate from the vortex meter 65. The instructions can also include those to perform the operation of verifying accuracy of the pressure and temperature compensated first density responsive to the determined second density from the measured mass flow rate, and/or verifying accuracy of the first mass flow rate responsive to the determined second mass flow rate. The instructions can also include those to perform the operation of providing data to display density 183, mass flow rate 184, and volumetric flow rate 182 to on a fluid characteristic display 35 positioned to receive density, volumetric flow rate, and mass flow rate, and providing data to display indicia indicating verified density 185 and verified mass flow rate 186. Note, the received second mass flow rate can be determined using a thermal sensor 149 positioned adjacent to the vortex shedding bluff body 63. Note also, according to various configurations, the thermal sensor 149 receives an obstructive flow of fluid which causes an error in the calculation/measurement of second mass flow rate. Correspondingly, the instructions can also include those to perform the operations of compensating for the error in the calculation/measurement of the second mass flow rate.

Another embodiment of the present invention can include a computer readable medium that is readable by a computer for measuring fluid flow characteristics in a pipeline having a set of instructions that, when executed by the computer, cause the computer to perform the operations of calculating a density indicative of flowing fluid density of the flowing fluid responsive to a received or measured volumetric flow rate and a thermal flow meter flow rate, and providing data to display, for example, in a fluid characteristic display 35, the volumetric flow rate 182, the density 183, and the mass flow rate 184, in their respective display fields. The vortex frequency shedding rate of fluid flowing in a pipeline 31 can be received or measured from a vortex meter 65 positioned adjacent a vortex shedding bluff body 63 positioned in the pipeline 31.

According to this embodiment, the vortex shedding body 65 can have an upstream surface 81, a plurality of downstream surfaces 83, a thermal sensor channel or fluid passage 95 extending between the upstream surface 81 and at least one of the downstream surfaces 83, and a thermal flow probe 141 positioned within the fluid passage 95. The thermal flow probe 149 can have an inlet port 143, an outlet port 145, and a thermal sensor channel 147 positioned therebetween and within the fluid passage way 95 positioned to form a second fluid passage way within the fluid passage way 95. The thermal flow probe 141 can also have at least one thermal sensor 149 positioned within the thermal sensor channel 147, if so configured, or within the passage way 95, if not so configured. The mass flow rate for the flowing fluid can be received from and/or measured with a thermal flow meter 97 positioned, for example, adjacent the vortex shedding bluff body 63. The thermal flow meter 97 can be electrically connected to the thermal sensor 149 and to an ambient temperature sensor such as, for example, sensor 111 co-positioned within the thermal sensor channel 147 (see FIG. 8) or sensor 113 (see FIG. 10) positioned to extend to the thermal sensor channel 147.

The instructions can include those to perform the operation of calculating a second density also indicative of flowing fluid density responsive to the received volumetric flow rate and a differential pressure meter flow rate signal. The differential pressure meter flow rate signal for the flowing fluid, for example, can be received from or measured with a differential pressure meter 89 positioned adjacent the vortex shedding bluff body 63. The instructions can also include those to perform the operations of comparing the first density to the second density to thereby verify accuracy of the first density, and providing data to display indicia indicating verified density. Advantageously, such indicia can be displayed in a density verified field 185 of a fluid characteristic display 35.

The instructions can also include those to perform the operation of calculating a second mass flow rate also indicative of flowing fluid mass flow rate responsive to the received volumetric flow rate and a differential pressure flow rate signal. The differential pressure flow rate signal can be provided by a differential pressure meter 89 which can be positioned adjacent the vortex shedding bluff body 63. The instructions can also include those to perform the operations of comparing the first mass flow rate to the second mass flow rate to thereby verify accuracy of the second mass flow rate, and providing data to display indicia indicating verified mass flow rate preferably in, for example, a corresponding mass flow rate verified field 185 of the fluid characteristic display 35.

The instructions can alternatively include those to perform the operations of determining a second density also indicative of flowing fluid density responsive to the volumetric flow rate and the differential pressure flow rate signal, and compensating the second density with a static pressure and an ambient temperature of the flowing fluid to thereby determine pressure and temperature compensated second density. The instructions can further include those to perform the operation of determining a second mass flow rate also indicative of flowing fluid mass flow rate responsive to the volumetric flow rate and the determined pressure and temperature compensated second density. Advantageously, the pressure and temperature compensated second density can be compared with the first density determined from the mass flow rate measured by the mass flow rate meter, e.g., thermal flow meter 97, to thereby verify accuracy of the first density. Also advantageously, the second mass flow rate determined from the pressure and temperature compensated density can also be compared with the first mass flow rate measured by the mass flow rate meter to thereby verify accuracy of the first mass flow rate. The instructions further include those to perform the operation of providing data to display indicia indicating verified first density and verified first mass flow rate, in their respective fields 185, 186.

The present application is related to U.S. patent application Ser. No. 10/856,492, filed on May 28, 2004, titled "System to Measure Density, Specific Gravity, and Flow Rate of Fluids, Meter, and Related Methods," which claims priority to and the benefit of U.S. Provisional Patent Application No. 60/495,743 filed on Aug. 15, 2003, both of which are incorporated herein by reference in their entireties.

In the drawings and specification, there have been disclosed embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims.

That claimed is:

1. A computer readable medium that is readable by a computer to measure fluid flow characteristics in a pipeline, the computer readable medium comprising a set of instructions that, when executed by the computer, cause the computer to perform the following operations:

calculating a density indicative of flowing fluid density responsive to a volumetric flow rate of fluid flowing in a pipeline adjacent a vortex shedding bluff body and a differential pressure flow rate signal for the flowing fluid indicating differential pressure between an upstream surface and at least one downstream surface of the vortex shedding bluff body, the differential pressure flow rate signal formed at least in part through determining a difference between pressure sensed at the upstream surface of the vortex shedding bluff body and pressure sensed at the at least one downstream surface;

calculating a mass flow rate indicative of flowing fluid mass flow rate responsive to the volumetric flow rate and the differential pressure flow rate signal; and providing data to a user thereof, the data representing the calculated density indicative of flowing fluid density and the calculated mass flow rate indicative of flowing fluid mass flow rate.

2. A computer readable medium as defined in claim 1, wherein the volumetric flow rate is received from a vortex meter positioned adjacent the vortex shedding bluff body;

wherein the vortex shedding bluff body is positioned in the pipeline and has an upstream surface including at least one total pressure inlet port and a downstream surface including at least one static pressure inlet port; and wherein the differential pressure flow rate signal is received from a differential pressure meter positioned adjacent the vortex shedding bluff body.

3. A computer readable medium as defined in claim 2, wherein the density is a first density, and wherein the mass flow rate is a first mass flow rate, the computer readable medium further comprising a set of instructions that, when executed by the computer, cause the computer to perform the following operations:
  measuring mass flow using a mass flow rate meter to thereby determine a second mass flow rate;
  calculating a second density of the flowing fluid responsive to the second mass flow rate and the volumetric flow rate; and
  comparing the first density with the second density responsive to the second density calculated from the second mass flow rate to thereby verify accuracy of the calculated first density.

4. A computer readable medium as defined in claim 2, wherein the density is a first density, and wherein the mass flow rate is a first mass flow rate, the computer readable medium further comprising a set of instructions that, when executed by the computer, cause the computer to perform the following operations:
  measuring mass flow using a thermal flow meter to thereby determine a second mass flow rate;
  calculating a second density also indicative of the flowing fluid density responsive to the second mass flow rate and the volumetric flow rate;
  comparing the first density to the second density, to thereby verify accuracy of the first density;
  comparing the first mass flow rate to the second mass flow rate, to thereby verify accuracy of the first mass flow rate; and
  providing data to a display responsive to the comparing operations, the data indicating the first density is verified and indicating the first mass flow rate is verified.

5. A computer readable medium as defined in claim 4, wherein the received second mass flow rate is determined using at least one thermal sensor positioned adjacent to the vortex shedding bluff body, wherein the at least one thermal sensor receives an obstructive flow of fluid, wherein the obstructive flow causes an error in the measurement of second mass flow rate, and wherein the computer readable medium further comprises instructions that, when executed by the computer, cause the computer to perform the operation of compensating for the error in the calculation of the second mass flow rate.

6. A computer readable medium as defined in claim 1, the computer readable medium further comprising a set of instructions that, when executed by the computer, cause the computer to perform the following operation:
  receiving an ambient temperature and a static pressure of the flowing fluid; and
  conditioning the density responsive to the ambient temperature and the static pressure to form a temperature and pressure compensated density.

7. A computer readable medium as defined in claim 6, wherein the density is a first density, and wherein the mass flow rate is a first mass flow rate, the computer readable medium further comprising a set of instructions that, when executed by the computer, cause the computer to perform the following operations:
  measuring mass flow to thereby determine a second mass flow rate;
  calculating a second density of the flowing fluid responsive to the second mass flow rate and the volumetric flow rate; and
  comparing the first density with the second density responsive to the second density calculated from the second mass flow rate to thereby verify accuracy of the pressure and temperature compensated first density.

8. A computer readable medium as defined in claim 7, the computer readable medium further comprising a set of instructions that, when executed by the computer, cause the computer to perform the following operation:
  comparing the first and second mass flow rates to thereby verify accuracy of the first mass flow rate determined from the pressure and temperature compensated density.

9. A computer readable medium as defined in claim 6, wherein the ambient temperature is received from an ambient temperature sensor electrically connected to a thermal flow meter positioned adjacent the vortex shedding bluff body, and wherein the static pressure is received from a differential pressure meter.

10. A computer readable medium that is readable by a computer to measure fluid flow characteristics in a pipeline, the computer readable medium comprising a set of instructions that, when executed by the computer, cause the computer to perform the following operations:
  determining a fluid flow rate and a volumetric flow rate responsive to a vortex frequency shedding rate of a vortex shedding bluff body;
  determining a specific gravity of the flowing fluid responsive to the volumetric flow rate and a differential pressure flow rate signal proportional to a differential pressure formed at least in part through determining a difference between pressure sensed an upstream surface of the vortex shedding bluff body and pressure sensed at a downstream surface of the vortex-shedding bluff body;
  determining a density of the flowing fluid responsive to determining the specific gravity; and
  providing data to a fluid characteristic display positioned to receive the density and the volumetric flow rate and positioned to display simultaneously the density and the volumetric flow rate, the data indicating the density and the volumetric flow rate.

11. A computer readable medium as defined in claim 10, the computer readable medium further comprising a set of instructions that, when executed by the computer, cause the computer to perform the following operations:
  compensating the density with a static pressure and an ambient temperature of the flowing fluid, to thereby determine the density compensated for by static pressure and temperature; and
  providing data to the fluid characteristic display to display the density on the fluid characteristic display, the data indicating the density compensated for by static pressure and temperature.

12. A computer readable medium as defined in claim 11, the computer readable medium further comprising a set of instructions that, when executed by the computer, cause the computer to perform the following operations:
  determining mass flow rate of the flowing fluid responsive to determining the pressure and temperature compensated density and volumetric flow rate to thereby determine the mass flow rate compensated for by pressure and temperature; and
  providing data to display the mass flow rate on the fluid characteristic display, the data indicating the mass flow rate compensated for by pressure and temperature.

13. A computer readable medium as defined in claim 10, wherein the density is a first density, and wherein the mass flow rate is a first mass flow rate, the computer readable medium further comprising a set of instructions that, when executed by the computer, cause the computer to perform the following operations:

receiving a second mass flow rate from a mass flow rate meter;

determining a second density of the flowing fluid responsive to the volumetric flow rate and the second mass flow rate; and verifying accuracy of the pressure and temperature compensated first density responsive to the determined second density.

14. A computer readable medium as defined in claim 13, the computer readable medium further comprising a set of instructions that, when executed by the computer, cause the computer to perform the operation of:

verifying accuracy of the first mass flow rate determined from the pressure and temperature compensated density, responsive to the second mass flow rate.

15. A computer readable medium as defined in claim 13, wherein the instructions that, when executed by the computer, cause the computer to perform the operation of verifying accuracy of the pressure and temperature compensated first density, further cause the computer to perform the operation of comparing the pressure and temperature compensated first density with the second density determined from the mass flow rate measured by the mass flow rate meter.

16. A computer readable medium as defined in claim 14, wherein the instructions that, when executed by the computer, cause the computer to perform the operation of verifying accuracy of the first mass flow rate determined from the pressure and temperature compensated density, further cause the computer to perform the operation of comparing the first mass flow rate determined from the pressure and temperature compensated density with the second mass flow rate measured by the mass flow rate meter.

17. A computer readable medium that is readable by a computer to measure fluid flow characteristics in a pipeline, the computer readable medium comprising a set of instructions that, when executed by the computer, cause the computer to perform the operations of:

calculating a density indicative of flowing fluid density of flowing fluid, responsive to a volumetric flow rate of fluid flowing in the pipeline received from a vortex meter positioned adjacent to a vortex shedding bluff body positioned in the pipeline, the vortex shedding bluff body having an upstream surface, a plurality of downstream surfaces, a thermal sensor fluid passageway extending between the upstream surface and at least one of the plurality of downstream surfaces, and at least one thermal sensor positioned within the thermal sensor fluid passageway and in communication with fluid flowing through the thermal sensor fluid passageway, and responsive to a mass flow rate for the flowing fluid measured by and received from a thermal flow meter positioned adjacent the vortex shedding bluff body and electrically connected to an ambient temperature sensor and the at least one thermal sensor; and providing data to a user thereof, the data representing the density indicative of the flowing fluid density of the flowing fluid.

18. A computer readable medium as defined in claim 17, wherein the density is a first density, the computer readable medium further comprising a set of instructions that, when executed by the computer, cause the computer to perform the following operations:

calculating a second density also indicative of flowing fluid density responsive to the volumetric flow rate and a differential pressure flow rate signal for the flowing fluid received from a differential pressure meter positioned adjacent the vortex shedding bluff body;

comparing the first density to the second density, to thereby verify accuracy of the first density; and providing data to a display, the data indicating the first density is verified.

19. A computer readable medium as defined in claim 17, wherein the mass flow rate is a first mass flow rate, the computer readable medium further comprising a set of instructions that, when executed by the computer, cause the computer to perform the following operations:

calculating a second mass flow rate also indicative of flowing fluid mass flow rate responsive to the volumetric flow rate and a differential pressure meter flow rate signal for the flowing fluid from a differential pressure meter positioned adjacent the vortex shedding bluff body;

comparing the first mass flow rate to the second mass flow rate, to thereby verify accuracy of the second mass flow rate; and providing data to a display, the data indicating the first mass flow rate is verified.

20. A computer readable medium as defined in claim 17, wherein the density is a first density, and wherein the mass flow rate is a first mass flow rate, the computer readable medium further comprising a set of instructions that, when executed by the computer, cause the computer to perform the following operations:

determining a second density also indicative of flowing fluid density, responsive to the volumetric flow rate and a differential pressure meter flow rate signal for the flowing fluid received from a differential pressure meter positioned adjacent the vortex shedding bluff body;

compensating the second density with a static pressure and an ambient temperature of the flowing fluid, to thereby determine pressure and temperature compensated second density;

determining a second mass flow rate also indicative of flowing fluid mass flow rate responsive to the volumetric flow rate and the pressure and temperature compensated second density;

comparing the pressure and temperature compensated second density with the first density determined from the mass flow rate measured by the thermal flow meter, to thereby verify accuracy of the first density;

comparing the second mass flow rate determined from the pressure and temperature compensated density with first mass flow rate measured by the thermal flow meter, to thereby verify accuracy of the first mass flow rate; and providing data to a display, the data indicating the first density is verified and indicating the first mass flow rate is verified.

\* \* \* \* \*